(12) United States Patent
Kasinath et al.

(10) Patent No.: US 11,471,287 B2
(45) Date of Patent: Oct. 18, 2022

(54) COMPOSITE ORTHOPAEDIC PROSTHESIS AND METHOD OF MAKING THE SAME

(71) Applicant: DEPUY IRELAND UNLIMITED COMPANY, Ringaskiddy (IE)

(72) Inventors: Rajendra K. Kasinath, Zionsville, IN (US); Steven P. Griffin, Franklin, MA (US); Jason B. Langhorn, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 5 days.

(21) Appl. No.: 17/095,132

(22) Filed: Nov. 11, 2020

(65) Prior Publication Data
US 2021/0137690 A1   May 13, 2021

Related U.S. Application Data

(60) Provisional application No. 63/070,963, filed on Aug. 27, 2020, provisional application No. 62/934,278, filed on Nov. 12, 2019.

(51) Int. Cl.
| | | |
|---|---|---|
| *A61F 2/38* | (2006.01) | |
| *A61F 2/30* | (2006.01) | |
| *C08L 59/02* | (2006.01) | |
| *C08L 79/08* | (2006.01) | |
| *C08L 81/06* | (2006.01) | |

(52) U.S. Cl.
CPC ........ *A61F 2/3859* (2013.01); *A61F 2/30965* (2013.01); *A61F 2/385* (2013.01); *A61F 2/389* (2013.01); *A61F 2002/3863* (2013.01); *C08L 59/02* (2013.01); *C08L 79/08* (2013.01); *C08L 81/06* (2013.01)

(58) Field of Classification Search
CPC .............................. A61F 2/389; A61F 2/3859
See application file for complete search history.

(56) References Cited

U.S. PATENT DOCUMENTS

| | | |
|---|---|---|
| 5,181,930 A | 6/1993 | Dumbleton et al. |
| 7,833,274 B2 | 11/2010 | Popoola et al. |
| 8,333,805 B2 | 12/2012 | Williams, III et al. |
| 8,829,096 B2 | 9/2014 | Jarman-Smith |
| 9,080,054 B2 | 7/2015 | Valentine et al. |
| 9,193,033 B2 | 11/2015 | Zhang et al. |
| 9,907,660 B2 | 3/2018 | Wang et al. |

(Continued)

FOREIGN PATENT DOCUMENTS

| | | |
|---|---|---|
| EP | 1836997 A1 | 9/2007 |
| EP | 2258319 A1 | 12/2010 |

(Continued)

OTHER PUBLICATIONS

International Search Report, International Application No. PCT/EP20207/081775, dated Mar. 25, 2021, 20 pages.

(Continued)

*Primary Examiner* — Jason-Dennis N Stewart
(74) *Attorney, Agent, or Firm* — Barnes & Thornburg LLP

(57) ABSTRACT

An orthopaedic prosthesis includes a femoral component comprising polymeric materials. The polymeric materials may include a polyaromatic ether or a polyacetal. The orthopaedic prosthesis may include a component having an articular layer and a support layer adjacent the articular layer. The support layer may include a reinforcement fiber. The orthopaedic prosthesis may be a knee prosthesis.

13 Claims, 14 Drawing Sheets

(56) References Cited

U.S. PATENT DOCUMENTS

| | | |
|---|---|---|
| 10,245,148 B2 | 4/2019 | Hanson |
| 2007/0255412 A1 | 11/2007 | Hajaj et al. |
| 2014/0035201 A1 | 2/2014 | Jarman-Smith et al. |
| 2015/0216667 A1 | 8/2015 | Monaghan |
| 2018/0055642 A1 | 3/2018 | Hanson |
| 2019/0029833 A1 | 1/2019 | Briscoe et al. |
| 2019/0358040 A1 | 11/2019 | Briscoe |

FOREIGN PATENT DOCUMENTS

| | | |
|---|---|---|
| EP | 3423008 B1 | 4/2019 |
| WO | 2009091802 A2 | 7/2009 |

OTHER PUBLICATIONS

Paul, J.P., Forces transmitted by joints in the human body. Proc Instn Meeh Engrs. 181, 8-15. 1966-67.

COMPOSITE ORTHOPAEDIC PROSTHESIS AND METHOD OF MAKING THE SAME

This application claims priority to U.S. Provisional Patent Application No. 62/934,278, filed Nov. 12, 2019, and 63/070,963, filed Aug. 27, 2020, the entire disclosure of each of which is hereby incorporated by reference.

TECHNICAL FIELD

The present disclosure relates generally to an orthopaedic prosthesis and more particularly to a composite orthopaedic prosthesis.

BACKGROUND

Joint arthroplasty is a well-known surgical procedure by which a diseased and/or damaged natural joint is replaced by a prosthetic joint. A typical knee prosthesis includes a patella prosthetic component, a tibial tray, a femoral component, and a bearing component positioned between the tibial tray and the femoral component. Femoral components are designed to be attached to a surgically-prepared distal end of a patient's femur. Tibial trays are designed to be attached to a surgically-prepared proximal end of a patient's tibia.

The femoral component and the tibial component are usually made of a biocompatible material such as metal alloys of cobalt-chrome or titanium. The bearing component disposed therebetween is usually formed of a plastic material like polyethylene.

SUMMARY

An orthopaedic implant comprises a femoral component configured to be coupled to a distal end of a patient's femur, the femoral component comprising a femoral condyle having (i) an articular layer that includes an articulation surface that is curved in a sagittal plane and configured to engage a tibial component, and (ii) a support layer that includes a bone-facing surface positioned opposite the articulation surface and configured to engage a distal end of a patient's femur. In some embodiments, the implant comprises a tibial component configured to be coupled to a proximal end of a patient's tibia, the tibial component including a concave surface shaped to engage the articulation surface of the femoral component.

In some embodiments, the articular layer of the femoral component is constructed of a material including a homopolymer or a copolymer, or composite including a blend of polymers.

In some embodiments, the support layer is constructed of a composite including (i) a homopolymer, a copolymer, or a mixture thereof and (ii) a reinforcement fiber.

Additional embodiments, features, and advantages of the disclosure will be apparent from the following detailed description and through practice of the disclosure. The compositions and materials of the present disclosure can be described as embodiments in any of the following enumerated clauses. It will be understood that any of the embodiments described herein can be used in connection with any other embodiments described herein to the extent that the embodiments do not contradict one another.

1. An orthopaedic knee prosthesis system, comprising:
a tibial component configured to be implanted on a proximal end of a patient's tibia, the tibial component including a concave bearing surface, and
a femoral component configured to be implanted on a distal end of a patient's femur, the femoral component comprising a femoral condyle having (i) an articular layer that includes an articulation surface that is curved in a sagittal plane and configured to articulate with the concave bearing surface of the tibial component, and (ii) a support layer that includes a bone-facing surface positioned opposite the articulation surface and configured to engage the distal end of the patient's femur,
wherein the articular layer of the femoral component comprises a polyetheretherketone (PEEK) homopolymer, and
wherein the support layer comprises (i) a reinforcement fiber and (ii) a homopolymer, a copolymer, or a mixture thereof.

2. The orthopaedic prosthesis system of clause 1, wherein the articular layer further comprises a polysulfone, a polyimide, or a mixture thereof.

3. The orthopaedic prosthesis system of clause 1 or 2, wherein the PEEK is about 75% to about 95% by weight of the articular layer.

4. The orthopaedic prosthesis system of any one of clauses 1-3, wherein the support layer comprises a polyaromatic ether homopolymer.

5. The orthopaedic prosthesis system of any one of clauses 1-3, wherein the support layer comprises a polyacetal copolymer.

6. The orthopaedic prosthesis system of clause 5, wherein the polyacetal copolymer is a polyoxymethylene copolymer.

7. The orthopaedic prosthesis system of any one of clauses 1-3, 5, or 6, wherein the support layer comprises at least about 80% polyoxymethylene.

8. The orthopaedic prosthesis system of any one of clauses 1-7, wherein the reinforcement fiber is a glass fiber or a carbon fiber.

9. An orthopaedic knee prosthesis, comprising:
a femoral component comprising a femoral condyle having (i) an articular layer that includes an articulation surface that is curved in a sagittal plane and configured to engage a tibial component, and (ii) a support layer that includes a bone-facing surface positioned opposite the articulation surface and configured to engage a distal end of a patient's femur,
wherein the articular layer is constructed of a composite including a blend of a polyetheretherketone (PEEK) homopolymer and a polysulfone, a polyimide, or a mixture thereof, and
wherein the articular layer has a yield strength of at least about 100 MPa.

10. The orthopaedic knee prosthesis of clause 9, wherein the articular layer is substantially free of fiber.

11. The orthopaedic knee prosthesis of clause 9 or 10, wherein the articular layer has a tensile modulus of at least about 4,000 MPa.

12. The orthopaedic knee prosthesis of any one of clauses 9-11, wherein the articular layer has an IZOD toughness of at least 5 J/m$^2$.

13. The orthopaedic knee prosthesis of any one of clauses 9-12, wherein the PEEK is about 75% to about 95% by weight of the articular layer.

14. An orthopaedic knee prosthesis, comprising:
a femoral component comprising a femoral condyle having (i) an articular layer that includes an articulation surface that is curved in a sagittal plane and configured to engage a tibial component, and (ii) a support layer that includes a bone-facing surface positioned opposite the articulation surface and configured to engage a distal end of a patient's femur, wherein the support layer comprises (i) a homopolymer, a copolymer, or a mixture thereof and (ii) a reinforcement fiber, wherein the support layer has tensile modulus of about 3,000 MPa to about 30,000 MPa.

15. The orthopaedic knee prosthesis of clause 14, wherein the support layer comprises a polyoxymethylene copolymer.

16. The orthopaedic knee prosthesis of clause 14, wherein the support layer comprises a polyaromatic ether.

17. An orthopaedic knee prosthesis, comprising:

a femoral component comprising a femoral condyle having (i) an articular layer that includes an articulation surface that is curved in a sagittal plane and configured to engage a tibial component, and (ii) a support layer that includes a bone-facing surface positioned opposite the articulation surface and configured to engage a distal end of a patient's femur, wherein the articular layer of the femoral component comprises a homopolymer, and wherein the support layer comprises a copolymer and a reinforcement fiber.

18. The orthopaedic knee prosthesis of clause 17, wherein the homopolymer of the articular layer is a polyaromatic ether or a polyacetal.

19. The orthopaedic knee prosthesis of clause 17 or 18, wherein the articular layer comprises a polyacetal copolymer.

20. The orthopaedic knee prosthesis of clause 19, wherein the polyacetal copolymer is a polyoxymethylene copolymer.

21. The orthopaedic knee prosthesis of clause 20, wherein the articular layer comprises at least about 80% polyoxymethylene copolymer.

22. The orthopaedic knee prosthesis of clause 18, wherein the polyaromatic ether is polyetheretherketone (PEEK).

23. The orthopaedic knee prosthesis of clause 22, wherein the PEEK is about 75% to about 95% by weight of the articular layer.

24. A method of making an implantable component for an orthopaedic prosthesis, comprising:

molding a first layer of polymeric material to second layer of polymeric material to form a composite, and forming the composite into a predetermined shape of the implantable component, wherein the implantable component has an articular layer and a support layer, wherein the articular layer comprises a homopolymer and the support layer comprises a polymer and a reinforcement fiber.

25. The method of clause 24, wherein the implantable component is an acetabular bearing which is adapted to be implanted into an acetabulum of a patient.

26. The method of clause 24, wherein the implantable component is a glenoid bearing which is adapted to be implanted into a glenoid of a patient.

27. The method of clause 24, wherein the implantable component is a tibial bearing which is adapted to be implanted into a tibia of a patient 28. The method of clause any one of clauses 24-27, wherein the articular layer comprises a polyetheretherketone (PEEK) homopolymer.

29. The method of clause 28, wherein the articular layer further comprises a polysulfone, a polyimide, or a mixture thereof.

30. The method of clause 28 or 29, wherein the PEEK is about 75% to about 95% by weight of the articular layer.

31. A method of making a femoral component of a knee prosthesis, comprising:

molding a first layer of polymeric material to second layer of polymeric material to form a composite, and forming the composite into a predetermined shape of the femoral component, wherein the femoral component has an articular layer and a support layer, wherein the articular layer comprises a homopolymer and the support layer comprises a polymer and a reinforcement fiber.

32. A method for forming a femoral component of a knee prosthesis, the method comprising:

molding together the articular layer and the support layer to form a composite, and forming the composite into a predetermined shape of the femoral component, wherein the articular layer is constructed a first polymeric material comprising a blend of homopolymers and the support layer comprises a second polymeric material that is different from the first polymeric material and comprises a reinforcement fiber.

33. The method of clause 32, wherein the first polymeric material comprises a polysulfone, a polyimide, or a mixture thereof.

34. The method of clause 32 or 33, wherein the homopolymer of the articular layer is a polyaromatic ether or a polyacetal.

35. The method of clause 34, wherein the polyaromatic ether is polyetheretherketone (PEEK).

36. The method of any one of clauses 32-35, wherein the support layer comprises a copolymer and a reinforcement fiber.

37. The method of clause 36, wherein the copolymer of the support layer is a polyacetal.

38. The method of clause 37, wherein the polyacetal is polyoxymethylene.

39. A method for forming a first component for orthopaedic implant, the method comprising molding together a composite of a first polymeric material comprising a polyaromatic ether and a second polymeric material comprising a polymer and a reinforcement fiber, and forming the composite into a predetermined shape of the first component, wherein the first polymeric material is configured to engage a second component of the orthopaedic implant and the second polymeric material is configured to engage bone.

40. The method of clause 39, wherein the first polymeric material comprises a homopolymer, a copolymer, or a mixture thereof.

41. The method of clause 40, wherein the homopolymer of the first polymeric material is a polyaromatic ether.

42. The method of any one of clauses 39-41, wherein the first polymeric material further comprises a polysulfone, a polyimide, or a mixture thereof.

43. The method of any one of clauses 39-42, wherein the polyaromatic ether is polyetheretherketone (PEEK).

44. The method of any one of clauses 39-43, wherein the polymer of the second polymeric material comprises is a copolymer.

45. The method of clause 44, wherein the copolymer of the second polymeric material is a polyacetal.

46. The method of clause 45, wherein the polyacetal is a polyoxymethylene.

47. The method of any one of clauses 39-46, wherein forming the composite comprises molding the composite into an acetabular bearing which is adapted to be implanted into an acetabulum of a patient.

48. The method of any one of clauses 39-46, wherein forming the composite comprises molding the composite into a glenoid bearing which is adapted to be implanted into a glenoid of a patient.

49. The method of any one of clauses 39-46, wherein forming the composite comprises molding the composite into a tibial bearing which is adapted to be implanted into a tibia of a patient.

50. An orthopaedic knee prosthesis, comprising:
a femoral component comprising a femoral condyle having an articulation surface that is curved in a sagittal plane and configured to engage a tibial component, and a bone-facing surface positioned opposite the articulation surface and configured to engage a distal end of a patient's femur,
wherein the femoral component comprises at least about 50% by weight of a homopolymer or a blend of a homopolymer and a polysulfone, a polyimide, or a mixture thereof, and
wherein the femoral component has a yield strength of at least about 100 MPa.

51. The orthopaedic knee prosthesis of clause 50, wherein the homopolymer is a polyaromatic ether or a polyacetal.

52. The orthopaedic knee prosthesis of clause 51, wherein the polyaromatic ether is polyetheretherketone (PEEK).

53. The orthopaedic knee prosthesis of clause 52, wherein the PEEK is about 75% to about 95% by weight of the femoral component.

54. The orthopaedic knee prosthesis of clause 51, wherein the polyacetal is a polyoxymethylene.

55. An orthopaedic prosthesis, comprising
a first component including an articular layer and a support layer, the articular layer configured to engage with a second component of the prosthesis and the support layer configured to engage a bone of a patient,
wherein the articular layer is constructed of a blend of a polyaryletherketone and a second polymer, and the support layer is constructed of a polymeric material.

56. The orthopaedic prosthesis of clause 55, wherein the second polymer of the articular layer is a polysulfone or a polyimide.

57. The orthopaedic prosthesis of clause 56, wherein the polysulfone is PPSU.

58. The orthopaedic prosthesis of clause 56, wherein the polyimide is PEI.

59. The orthopaedic prosthesis of any one of clauses 55-58, wherein the polyaryletherketone is at least about 80% by weight, preferably at least about 85% by weight.

60. The orthopaedic prosthesis of any one of clauses 55-59, wherein the second polymer is present at less than about 20%, preferably less than about 15% by weight.

61. The orthopaedic prosthesis of any one of clauses 55-60, wherein the second polymer is present at about 5% to about 20% by weight.

62. The orthopaedic prosthesis of any one of clauses 55-61, wherein the support layer comprises a reinforcement fiber or a reinforcement particle.

63. The orthopaedic prosthesis of any one of clauses 55-62, wherein the support layer comprises a reinforcement fiber, preferably a glass fiber or a carbon fiber.

64. The orthopaedic prosthesis of any one of clauses 55-62, wherein the support layer comprises a reinforcement particle, preferably barium sulfate.

65. The orthopaedic prosthesis of any of clauses 55-62, wherein the support layer is devoid of a reinforcement fiber or a reinforcement particle.

66. The orthopaedic prosthesis of any one of clauses 55-65, wherein the articular layer is devoid of a reinforcement fiber or a reinforcement particle.

67. The orthopaedic prosthesis of any one of clauses 55-66, wherein the articular layer has a yield strength of at least about 100 MPa, preferably at least about 102 MPa.

68. The orthopaedic prosthesis of any one of clauses 55-67, wherein the articular layer has a tensile modulus of at least 3,000 MPa, preferably at least 4,000 MPa.

69. The orthopaedic prosthesis of any one of clauses 55-68, wherein the articular layer has a compressive yield of at least about 100 MPa, preferably at least about 105 MPa, or more preferably at least about 110 MPa.

70. The orthopaedic prosthesis of any one of clauses 55-69, wherein the articular layer has an IZOD toughness of at least 5 $J/m^2$ or about 5.3 $J/m^2$ to about 8 $J/m^2$.

71. The orthopaedic prosthesis of any one of clauses 55-70, wherein the wear rate of the articular layer is less than about 10, preferably less than about 6, or preferably less than about 4 mg/million cycles (MC).

72. The orthopaedic prosthesis of any one of clauses 55-71, wherein the first component is an acetabular component which is adapted to be implanted into an acetabulum of a patient.

73. The orthopaedic prosthesis of any one of clauses 55-71, wherein the first component is a glenoid component which is adapted to be implanted into a glenoid of a patient.

74. The orthopaedic prosthesis of any one of clauses 55-71, wherein the first component is a tibial component which is adapted to be implanted into a tibia of a patient.

75. The orthopaedic prosthesis of any one of clauses 55-71, wherein the first component is a femoral component which is adapted to be implanted into a femur of a patient.

BRIEF DESCRIPTION OF THE DRAWINGS

The detailed description particularly refers to the following figures, in which.

DETAILED DESCRIPTION OF THE DRAWINGS

Figure 1:
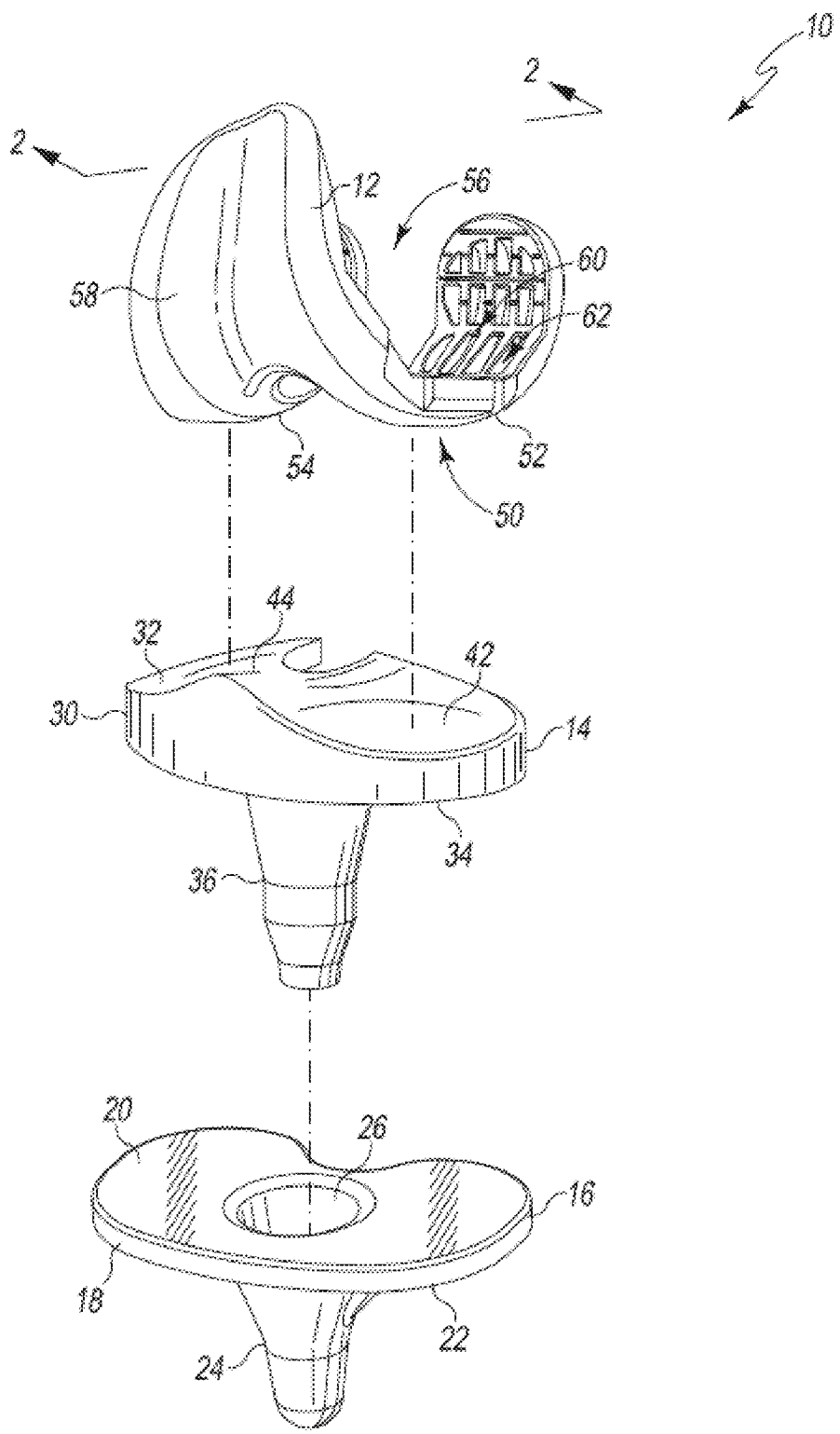
FIG. 1 is an exploded perspective view of an orthopaedic knee prosthesis.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, in one embodiment, an orthopaedic knee prosthesis 10 includes a femoral component 12, a tibial bearing 14, and a tibial tray 16. The femoral component 12 is configured to articulate with the tibial bearing 14, which is configured to be coupled with the tibial tray 16. In the illustrative embodiment of FIG. 1, the tibial bearing 14 is embodied as a rotating or mobile tibial bearing and is configured to rotate relative to the tibial tray 16 during use. However, in other embodiments, the tibial bearing 14 may be embodied as a fixed tibial bearing, which may be limited or restricted from rotating relative to the tibial tray 16.

The tibial tray 16 is configured to be secured to a surgically-prepared proximal end of a patient's tibia (not shown). The tibial tray 16 may be secured to the patient's tibia via use of bone adhesive or other attachment methods. The tibial tray 16 includes a platform 18 having a top surface 20 and a bottom surface 22. Illustratively, the top surface 20 is generally planar. The tibial tray 16 also includes a stem 24 extending downwardly from the bottom surface 22 of the platform 18. A cavity or bore 26 is defined in the top surface 20 of the platform 18 and extends downwardly into the stem 24. The bore 26 is formed to receive a complimentary stem of the tibial insert 14 as discussed in more detail below.

As discussed above, the tibial bearing 14 is configured to be coupled with the tibial tray 16. The tibial bearing 14 includes a platform 30 having an upper bearing surface 32 and a bottom surface 34. In the illustrative embodiment wherein the tibial bearing 14 is embodied as a rotating or mobile tibial bearing, the bearing 14 includes a stem 36 extending downwardly from the bottom surface 32 of the platform 30. When the tibial bearing 14 is coupled to the tibial tray 16, the stem 36 is received in the bore 26 of the tibial tray 16. In use, the tibial bearing 14 is configured to rotate about an axis defined by the stem 36 relative to the tibial tray 16. In embodiments wherein the tibial bearing 14 is embodied as a fixed tibial bearing, the bearing 14 may or may not include the stem 22 and/or may include other devices or features to secure the tibial bearing 14 to the tibial tray 16 in a non-rotating configuration.

The upper bearing surface 32 of the tibial bearing 14 includes a medial bearing surface 42 and a lateral bearing surface 44. The medial and lateral bearing surfaces 42, 44 are configured to receive or otherwise contact corresponding medial and lateral condyles of the femoral component 12 as discussed in more detail below. As such, each of the bearing surface 42, 44 has a concave contour.

The femoral component 12 is configured to be coupled to a surgically-prepared surface of the distal end of a patient's femur (not shown). The femoral component 12 may be secured to the patient's femur via use of bone adhesive or other attachment methods. The femoral component 12 includes an outer, articulating surface 50 having a pair of medial and lateral condyles 52, 54. The condyles 52, 54 are spaced apart to define an intracondyle opening 56 therebetween. In use, the condyles 52, 54 replace the natural condyles of the patient's femur and are configured to articulate on the corresponding bearing surfaces 42, 44 of the platform 30 of the tibial bearing 14.

The illustrative orthopaedic knee prosthesis 10 of FIG. 1 is embodied as a posterior cruciate-retaining knee prosthesis. That is, the femoral component 12 is embodied as a posterior cruciate-retaining knee prosthesis and the tibial bearing 14 is embodied as a posterior cruciate-retaining tibial bearing 14. However, in other embodiments, the orthopaedic knee prosthesis 10 may be embodied as a posterior cruciate-sacrificing knee prosthesis.

Figure 2:
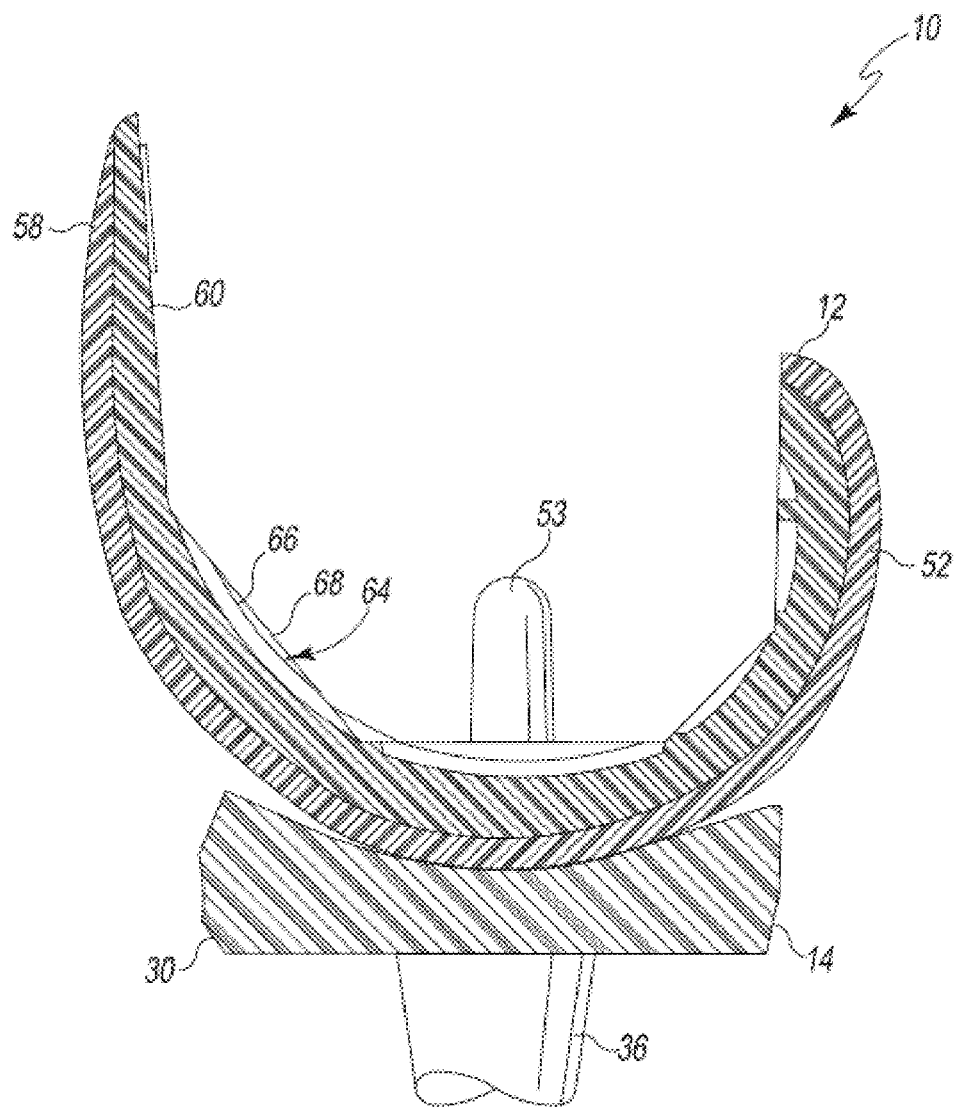
FIG. 2 is a cross-sectional view of the femoral component and tibial bearing of FIG. 1 taken generally along the line 2-2 of FIG. 1, as viewed in the direction of the arrows.

Referring now to FIG. 2, the femoral component 12 is configured to articulate on the tibial bearing 14 during use. Each condyle 52, 54 of the femoral component 12 includes a condyle surface, which is convexly curved in the sagittal plane and configured to contact the respective bearing surface 42, 44.

The femoral component 12 includes an articular layer 58 and a support layer 60, as shown in FIG. 2. The articular layer 58 is configured to form all or part of the articulating surface 50. The support layer 60 is configured to form all or part of a bone-facing surface 62. The support layer 60 is configured to be coupled to a surgically-prepared surface of the distal end of a patient's femur (not shown). The articular layer 58 is secured to the support layer 60.

A polymer or a blend of polymers is preferably used to construct the layers 58, 60. As used herein, the term "polymer" is intended to mean any polymeric material which may be implanted into a patient. A specific example of such a polymer is the polyaryletherketone (PAEK) family, the polysulfone family, the polyimide family, and the polyacetal family. The term "polyaryletherketone," as defined herein, includes polyetheretherketone (PEEK), polyetherketone, and polyetherketoneetherketoneketone or any other type of polyaryletherketone used in the construction of a prosthetic implant. The term "polymer" is also intended to include both homopolymers and copolymers.

It should be appreciated that, as used herein, the term "layer" is not intended to be limited to a "thickness" of material positioned proximate to another similarly dimensioned "thickness" of material, but rather is intended to include numerous structures, configurations, and constructions of material. For example, the term "layer" may include a portion, region, or other structure of material which is positioned proximate to another portion, region, or structure of differing material. For instance, an articular surface may define a first "layer" of material, whereas a support layer that contacts the articular layer may define a second "layer" of material.

In illustrative embodiments, the articular layer 58 and the support layer 60 are molded together. In illustrative embodiments, the articular layer 58 and the support layer 60 together are about 3 mm to about 8 mm thick. In illustrative embodiments, the articular layer 58 and the support layer 60 together are about 5 mm thick. In illustrative embodiments, the articular layer 58 has a thickness that is about 0.1 mm to 2 mm thick.

In illustrative embodiments, the articular layer 58, the support layer 60, or both the articular layer 58 and the support layer 60 are constructed of polymeric materials. In some embodiments, the articular layer 58 comprises a homopolymer, a copolymer, or a mixture thereof. In some embodiments, the articular layer 58 comprises more than one homopolymer. In some embodiments, the articular layer 58 consists or consists essentially of a homopolymer. In some embodiments, the articular layer 58 consists or consists essentially of a homopolymer and a copolymer.

In some embodiments, the articular layer 58 is constructed of a composite including a first polymer and a second polymer. In some embodiments, the first polymer is a homopolymer. In some embodiments, the second polymer is a homopolymer. In some embodiments, the articular layer 58 consists or consists essentially of a first homopolymer and a second homopolymer. In illustrative embodiments, the articular layer 58 is devoid of barium sulfate.

In some embodiments, the homopolymer of the articular layer 58 is a polyaromatic ether, a polyacetal, or a mixture thereof. Illustrative polyaromatic ethers include polyetheretherketone or more commonly referred to as "PEEK." In some examples, the articular layer 58 includes KETASPIRE KT-880 available from SOLVAY SPECIALTY POLYMERS. In some embodiments, the polyacetal is polyoxymethylene or more commonly referred to as "POM." Illustrative polyoxymethylene homopolymers include KEP H100 available from KEP Americas. In some embodiments, the polyacetal or the polyaromatic ether is the first homopolymer.

In some embodiments, the articular layer 58 includes a homopolymer present at a particular percentage by weight. In illustrative embodiments, the articular layer 58 comprises at least about 50%, at least about 60%, at least about 70%, at least about 75%, at least about 80%, at least about 85%, at least about 90%, or at least about 95% by weight first homopolymer. In some embodiments, the homopolymer is about 100% by weight of the articular layer 58. In illustrative embodiments, the homopolymer is POM. In illustrative embodiments, the homopolymer is PEEK.

In some embodiments, the homopolymer of the articular layer 58 is a polyimide or a polysulfone. In some embodiments, the polyimide may be a polyetherimide, commonly referred to as "PEI." Exemplary PEI includes Ultem HU1000 from Sabic, and COLORRX PEI-1600RX available from LTL COLOR COMPOUNDERS, LLC. In some embodiments, the polysulfone may be a polyphenylsulfone, commonly referred to as "PPSU." Exemplary PPSU includes RADEL R-5800 NT available from SOLVAY SPECIALTY POLYMERS. In some embodiments, the polyimide or the polysulfone is the second homopolymer.

In some embodiments, the articular layer 58 is constructed of a composite including a homopolymer blend of at least 2 or at least 3 homopolymers. In some embodiments, the homopolymer blend includes a polyaromatic ether and a polyimide. In some embodiments, the homopolymer blend consists or consists essentially of a polyaromatic ether such as PEEK and PEI. In some embodiments, the homopolymer blend includes a polyaromatic ether and a polysulfone. In some embodiments, the homopolymer blend consists or consists essentially a polyaromatic ether such as PEEK and PPSU.

In some embodiments, the articular layer 58 is constructed of a composite including a homopolymer blend including a first homopolymer and a second homopolymer. In illustrative embodiments, the articular layer 58 includes (by weight %) about 50% of a first homopolymer and about 50% of a second homopolymer, about 60% of a first homopolymer and about 40% of a second homopolymer, about 70% of a first homopolymer and about 30% of a second homopolymer, about 75% of a first homopolymer and about 25% of a second homopolymer, about 80% of a first homopolymer and about 20% of a second homopolymer, about 85% of a first homopolymer and about 15% of a second homopolymer, about 88% of a first homopolymer and about 12% of a second homopolymer, about 90% of a first homopolymer and about 10% of a second homopolymer, or about 95% of a first polymer and about 5% of a second homopolymer. In illustrative embodiments, the first homopolymer can be a polyaromatic ether and the second homopolymer can be a polysulfone or a polyimide. In illustrative embodiments, the first homopolymer is PEEK. In illustrative embodiments, the second homopolymer is PPSU or PEI. In some embodiments, the first homopolymer is PEEK and the second homopolymer is PPSU. In some embodiments, the first homopolymer is PEEK and the second homopolymer is PEI.

In some embodiments, the homopolymer is a blend of PEI and PEEK. This may by denoted as PEI/PEEK. In some embodiments, the PEI/PEEK homopolymer blend includes at least about 5% or at least about 10% PEI by weight. In some embodiments, the PEI/PEEK homopolymer blend includes up to about 90% or up to about 95% PEEK by weight. Some embodiments include about 5% PEI and about 95% PEEK, about 10% PEI and about 90% PEEK, about 12% PEI and about 88% PEEK, about 15% PEI and about 85% PEEK, and about 20% PEI and about 80% PEEK.

In some embodiments, the homopolymer blend is a combination of PPSU and PEEK. This may be denoted as PPSU/PEEK. In some embodiments, the PPSU/PEEK homopolymer blend includes at least about 5% or at least about 10% by weight PPSU. In some embodiments, the PPSU/PEEK homopolymer blend includes less than about 20% or less than about 15% by weight PPSU. In some embodiments, the PPSU/PEEK homopolymer blend includes up to about 85%, up to about 90% by weight PEEK, or up to about 95% by weight PEEK. Some embodiments include about 5% PPSU and about 95% PEEK, about 10% PPSU and about 90% PEEK, about 12% PPSU and about 88% PEEK, about 15% PPSU and about 85% PEEK, and about 20% PPSU and about 80% PEEK.

In some embodiments, the articular layer 58 has a yield strength as measured by ASTM D638. In an illustrative embodiment, the yield strength of the articular layer 58 is in a range from about 100 MPa to about 220 MPa. In some embodiments, the yield strength of the articular layer 58 is at least about 100 MPa, at least about 102 MPa, or at least about 103 MPa. In some embodiments, the yield strength of the articular layer 58 is at least about 100 MPa or at least about 125 MPa. In some embodiments, the yield strength is about 100 MPa to about 150 MPa or about 102 MPa to about 150 MPa. In some embodiments, the yield strength is about 115 MPa to about 220 MPa, about 150 MPa to about 220 MPa, or about 175 MPa to about 220 MPa. In some embodiments, the articular layer 58 has a yield strength of about 99 MPa to about 104.5 MPa, about 100 MPa to about 103.5 MPa, or about 102 MPa to about 104 MPa. In some embodiments, the articular layer 58 has a yield strength of about 189 MPa to about 191.5 MPa, about 189.5 MPa to about 191 MPa, or about 189.5 MPa to about 190.5 MPa. In some embodiments, the articular layer 58 has a yield strength of about 199 MPa to about 201 MPa, about 199.5 to about 200.5 MPa, or about 200 MPa.

In some embodiments, the articular layer 58 has a Tensile Modulus as measured by ASTM D638. In an illustrative embodiment, the Tensile Modulus of the articular layer 58 is in a range of about 3,000 MPa to about 30,000 MPa or about 3,500 MPa to about 30,000 MPa. In some embodiments, the Tensile Modulus of the articular layer 58 is at least about 3,000 MPa, at least about 4,000 MPa, at least about 4,100 MPa, or at least about 4,300 MPa. In some embodiments, the articular layer 58 has a Tensile Modulus of about 3,000 MPa to about 30,000 MPa, about 3,000 MPa to about 10,000 MPa, about 4,000 MPa to about 10,000 MPa, about 4,100 MPa to about 10,000 MPa, about 4,200 MPa to about 10,000 MPa, or about 4,500 MPa to about 6,000 MPa. In some embodiments, the articular layer 58 has a Tensile Modulus of about 5,500 MPa to about 24,000 MPa, about 5,500 MPa to about 18,000 MPa, about 5,500 MPa to about 13,000 MPa, or about 5,500 MPa to about 10,800 MPa. In some embodiments, the articular layer 58 has a Tensile Modulus of about 6,800 MPa to about 10,500 MPa, about 6,900 MPa to about 7,900 MPa, or about 6,900 MPa to about 7,700 MPa.

In some embodiments, the articular layer 58 has an IZOD impact toughness as measured by ASTM D4812. Illustratively, the articular layer 58 has an IZOD impact toughness of at least 5 J/m². In illustrative embodiments, the toughness of the articular layer 58 is in a range of about 5 J/m² to about 10 J/m², about 5.2 J/m² to about 10 J/m², about 5.2 J/m² to about 8 J/m², or about 5.3 J/m² to about 8 J/m².

In some embodiments, the articular layer 58 has a compressive yield as measured by ASTM D695. Illustratively, the articular layer 58 has a compressive yield of at least about 50 MPa, at least about 110 MPa, at least about 115 MPa, or at least about 120 MPa. In some embodiments, the compressive yield is about 50 MPa to about 150 MPa or about 110 MPa to about 150 MPa.

In some embodiments, the articular layer 58 has fatigue behavior as measured by using an ASTM D3479/D3479M Tension-tension fatigue test. In some embodiments, each cycle of the fatigue test at the given stress level is performed at 2 Hertz and to 5 million cycles. In some embodiments, an articular layer 58 constructed of a blend of homopolymers or a blend of PEEK with another polymer performs better than an articular layer 58 constructed of a single homopolymer. In some embodiments, the fatigue strength is at least about 60 MPa or at least about 70 MPa.

The wear rate of the articular layer 58 can be measured by contacting the articular layer 58 with a material. In exemplary embodiments, the wear rate of the articular layer 58 is measured by contacting the articular layer 58 with a polyethylene such as cross-linked ultra-high molecular weight polyethylene, available as XLK ultra-high molecular weight polyethylene. In some embodiments, the articular layer 58 has a wear rate of less than about 10, less than about 8, less than about 6, or less than about 4 mg/million cycles (MC). In some embodiments, the wear rate of the articular layer 58 is in a range of about 0.5 mg/MC to about 10 mg/MC. In some embodiments, the wear rate is about 1.5 mg/MC to about 7 mg/MC or about 1.5 mg/MC to about 4 mg/MC.

In illustrative embodiments, the articular layer 58 is secured to the support layer 60. The support layer 60 is configured to extend between the articular layer 58 and a patient's surgically repaired femur.

In illustrative embodiments, the support layer 60 is constructed of a composite including (i) a homopolymer, a copolymer, or a mixture thereof and (ii) a reinforcement fiber.

In some embodiments, the support layer 60 includes a homopolymer, a copolymer, or a mixture thereof. In some embodiments, the support layer 60 includes a homopolymer. In some embodiments, the support layer 60 includes a copolymer. In some embodiments, the support layer 60 is constructed of a composite including a homopolymer and a reinforcement fiber. In some embodiments, the support layer 60 is constructed of a composite including a copolymer and a reinforcement fiber. In some embodiments, the support layer 60 is constructed of a composite that consists or consists essentially of a homopolymer and a reinforcement fiber. In some embodiments, the support layer 60 is constructed of a composite that consists or consists essentially of a copolymer and a reinforcement fiber. In some embodiments, the support layer 60 includes a reinforcement particle such as barium sulfate. In some embodiments, the supper layer 60 is devoid of a reinforcement fiber or a reinforcement particle.

In some embodiments, the support layer 60 includes a copolymer. In some embodiments, the support layer 60 includes a polyacetal. In some embodiments, the support layer 60 includes a polyacetal copolymer. In some embodiments, the copolymer polyacetal is a polyoxymethylene copolymer or commonly referred to as "POM." Exemplary POM co-polymers include Hostaform, MT12U03 or MT2U06 available from CELANESE.

In illustrative embodiments, the support layer 60 includes at least about 50%, at least about 60%, at least about 70%, at least about 75%, at least about 80%, at least about 85%, at least about 90%, or at least about 95% by weight copolymer. In these illustrative embodiments, the copolymer can be a polyacetal such as POM.

In some embodiments, the support layer 60 includes a homopolymer. In some embodiments, the support layer 60 includes a polyaromatic ether. In some embodiments, the support layer 60 includes PEEK.

In illustrative embodiments, the support layer 60 includes at least about 50%, at least about 60%, at least about 70%, at least about 75%, at least about 80%, at least about 85%, at least about 90%, or at least about 95% by weight homopolymer. In these illustrative embodiments, the homopolymer can be a polyaromatic ether such as PEEK.

In some embodiments, the support layer 60 includes reinforcement fibers. The reinforcement fiber may be distributed throughout the support layer 60. Illustrative reinforcement fibers include glass fiber or carbon fiber. In some embodiments, the support layer 60 includes carbon fiber reinforced (CFR) PEEK. Illustrative CFR PEEK is available from SOLVAY SPECIALTY POLYMERS. In some embodiments, the support layer 60 includes glass fiber reinforced (GFR) polyacetal. In other embodiments, the support layer 60 is devoid of reinforcement fibers.

In some embodiments, the support layer 60 has a yield strength as measured by ASTM D 638. In an illustrative embodiment, the yield strength of the support layer 60 is in a range from about 50 MPa to about 150 MPa. In some embodiments, the yield strength of the support layer 60 is at least about 50 MPa or at least about 75 MPa. In some embodiments, the yield strength is about 50 MPa to about 200 MPa, about 50 MPa to about 150 MPa, or about 50 MPa to about 125 MPa.

In some embodiments, the support layer 60 has a Young's Modulus as measured by ASTM D 638. In an illustrative embodiment, the Young's Modulus of the support layer 60 is in a range of about 3,500 MPa to about 30,000 MPa. In some embodiments, the Young's Modulus of the support layer 60 is at least about 3,000 MPa, at least about 5,000 MPa, at least about 10,000 MPa, or at least about 15,000 MPa. In some embodiments, the support layer 60 has a Young's Modulus of about 3,500 MPa to about 30,000 MPa, about 5,500 MPa to about 25,000 MPa, or about 5,500 MPa to about 23,000 MPa.

In other embodiments, the femoral component 12 is constructed of a single composition such that the femoral component 12 is monolithic. In illustrative embodiments, the femoral component 12 is constructed of a single composition comprising a homopolymer, a copolymer, or a mixture thereof. In some embodiments, the femoral component 12 is constructed of a single composition comprising a blend of at least two homopolymers. In some embodiments, the homopolymer is a polyaromatic ether, preferably PEEK. In some embodiments, the homopolymer is a polyacetal, preferably POM. In some embodiments, the femoral component 12 is constructed of a single composition comprising a blend of a polyaromatic ether, preferably PEEK, and a second homopolymer, preferably PPSU, PEI, or a mixture thereof. Illustratively, the femoral component constructed of a single composition does not include a reinforcement fiber.

In an illustrative process, the femoral component 12 can be constructed by molding together the articular layer 58 and the support layer 60. In some embodiments, the articular layer 58 is over-molded onto the support layer 60. The process could be injection molding, or compression molding. The interfacial adhesion between layers may be enhanced during the process, either through physical interlocking designs and/or chemically leveraging chemical mixability between polymers, for examples between PEEK and PEI.

In some embodiments, the process for forming an orthopaedic implant comprises molding material to form the support layer 60. In illustrative embodiments, the process further comprises over-molding material to form the articular layer 58 onto the support layer 60 to form a molded blank. In illustrative embodiments, the process further comprises finishing the molded blank into the orthopaedic implant. In illustrative embodiments, the process forms a femoral component of a knee implant. In some embodiments, the composite forms an acetabular bearing which is adapted to be implanted into an acetabulum of a patient. In other illustrative embodiments, the composite forms a glenoid bearing which is adapted to be implanted into a glenoid of a patient. In other illustrative embodiments, the composite forms a tibial bearing which is adapted to be implanted into a tibia of a patient.

In an embodiment, an orthopaedic implant includes an articular layer 58 and a support layer 60 arranged to contact the articular layer 58. The articular 58 is constructed of a blend of a polyaryletherketone and a polyimide, preferably PEEK and PEI. The polyaryletherketone, preferably PEEK, is at least 80% and preferably at least 85% by weight and the polyimide, preferably PEI, is present at less than 20% preferably less than 15% by weight. The articular layer 58 has a yield strength of at least about 100 MPa, at least about 102 MPa. The articular layer 58 has a tensile modulus of at least 3,000 MPa, preferably at least 4,000 MPa, and preferably at least 4,100 MPa. The articular layer 58 has a compressive yield of at least about 110 MPa, preferably at least about 115 MPa, or more preferably at least about 120 MPa. The IZOD toughness is at least 5 $J/m^2$ or about 5.3 $J/m^2$ to about 8 $J/m^2$. The wear rate is less than about 10, preferably less than about 6, or preferably less than about 4 mg/million cycles (MC). The support layer 60 is constructed of a polymer, such as a polyacetal or a polyaryletherketone, and optionally contains a reinforcement fiber such as a carbon fiber or a glass fiber or a reinforcement particle such as barium sulfate.

In an embodiment, an orthopaedic implant includes an articular layer 58 and a support layer 60 arranged to contact the articular layer 58. The articular 58 is constructed of a blend of a polyaryletherketone and a polysulfone, preferably PEEK and PPSU. The polyaryletherketone, preferably PEEK, is at least 80% and preferably at least 85% by weight and the polysulfone, preferably PPSU, is present at less than 20% preferably less than 15% by weight. The articular layer 58 has a tensile modulus of at least 3,000 MPa, preferably at least 3,500 MPa. The articular layer 58 has a compressive yield of at least about 100 MPa, preferably at least about 105 MPa, or more preferably at least about 110 MPa. The IZOD toughness is at least 5 $J/m^2$ or about 5.3 $J/m^2$ to about 8 $J/m^2$. The wear rate is less than about 10, preferably less than about 6, or preferably less than about 4 mg/million cycles (MC). The support layer 60 is constructed of a polymer, such as a polyacetal or a polyaryletherketone, and optionally contains a reinforcement fiber such as a carbon fiber or a glass fiber or a reinforcement particle such as barium sulfate.

EXAMPLES

Example 1

Tensile Properties

Five different types of test coupons were prepared and their tensile properties tested. The results are shown in FIGS. 3-6. The formulations are shown below. The percentages, when present, are in weight percent. 10 coupons of each type of formulation were prepared and tested. Tensile testing was performed according to the methods specified in ASTM D638 with Type 1 dog-bone specimens. Displacement rate was 5 mm/min until displacement reached 0.5 mm, and thereafter samples were tested to failure at a rate of 50.5 mm/min.

The PEEK coupon was formed from molding Ketaspire KT-880 NT.

The POM coupon was formed from molding Hostaform MT12U03.

The 90PEEK/10PEI coupon was formed by blending and molding 90% Ketaspire KT-880 NT with 10% ColorRX PEI 1600 RX.

The 80PEEK/20PEI coupon was formed by blending and molding 80% Ketaspire KT-880 NT with 20% ColorRX PEI 1600 RX.

The 90PEEK/10PPSU coupon was formed by blending 90% Ketaspire KT-880 NT+10% Radel R5800 NT.

The 95PEEK/5PEI coupon was formed by blending and molding 95% Ketaspire KT-880 NT with 5% ColorRX PEI 1600 RX.

Figure 3:
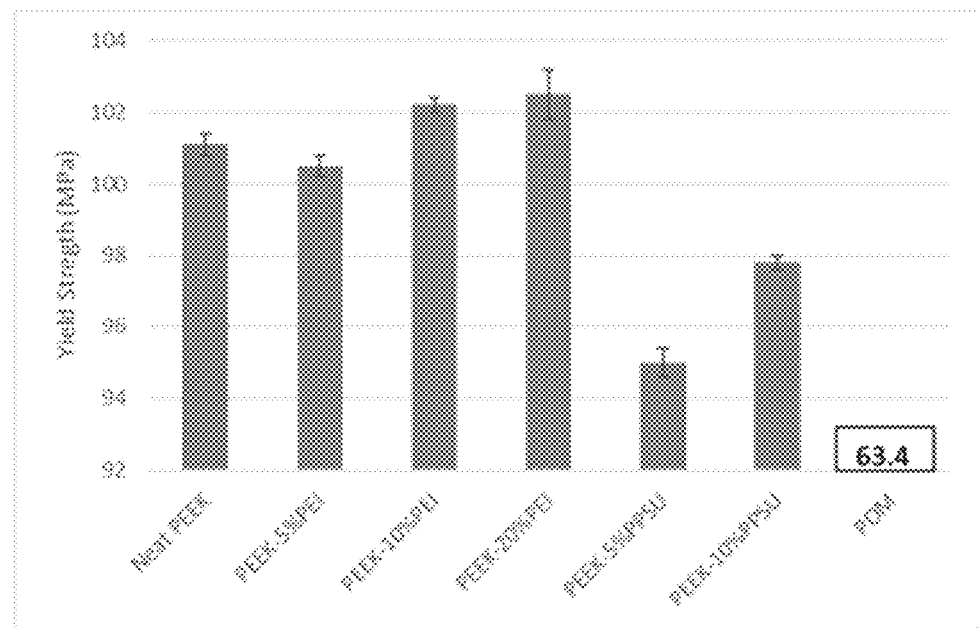
FIG. 3 is a graph showing the tensile strength of the various compositions disclosed herein.

The tensile strength of the coupons was measured according to ASTM D638. The results are shown in FIG. 3.

Figure 4:
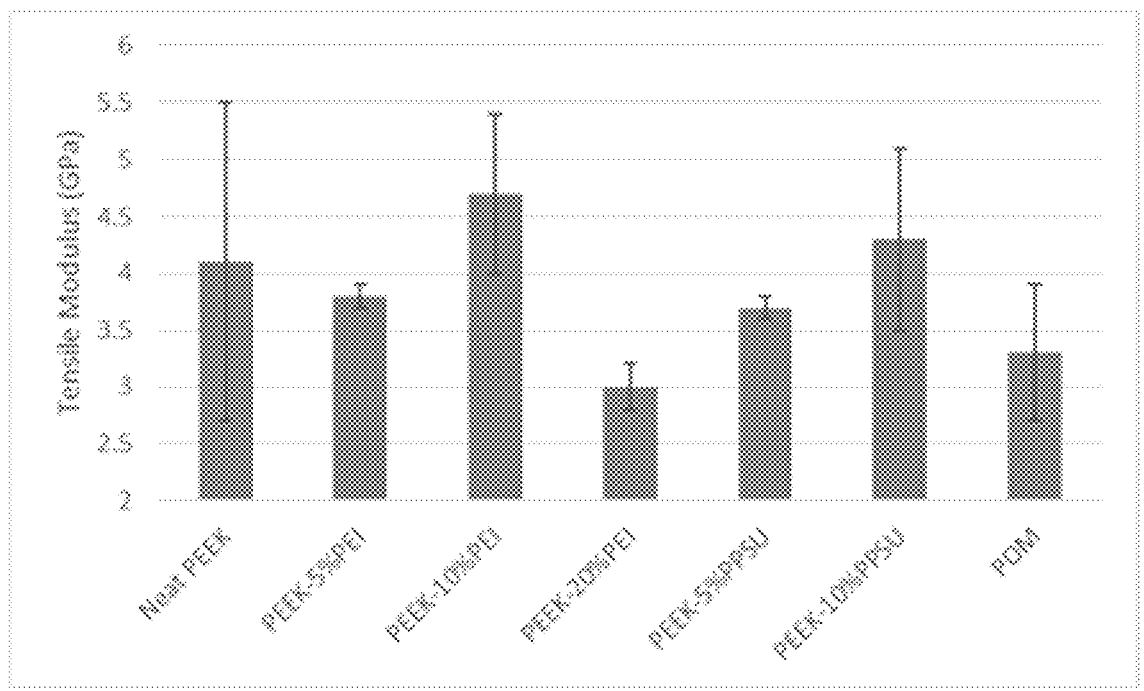
FIG. 4 is a graph showing the tensile modulus of the various compositions disclosed herein.

The tensile modulus of the coupons was measured according to ASTM D638. The results are shown in FIG. 4.

Figure 5:
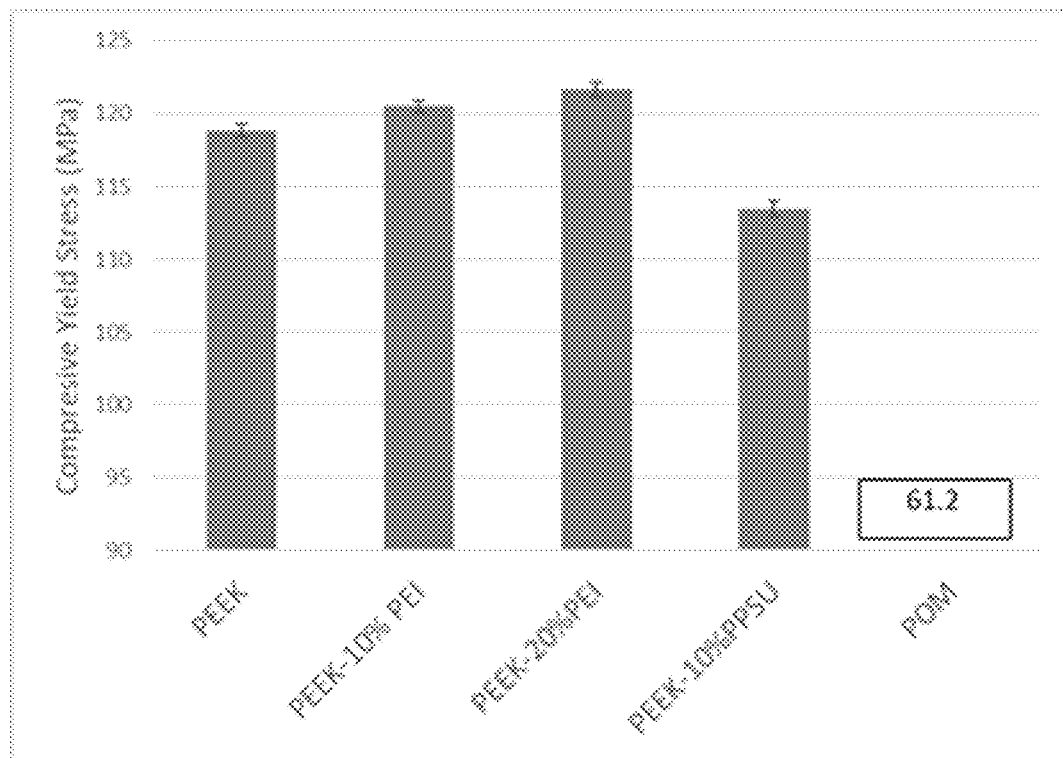
FIG. 5 is a graph showing the compressive strength of the various compositions disclosed herein.

The compressive strength of the coupons was measured according to ASTM D695. The loading rate was 1.3 mm/min and the test was carried out until 20% strain was reached. The results are shown in FIG. 5.

Figure 6:
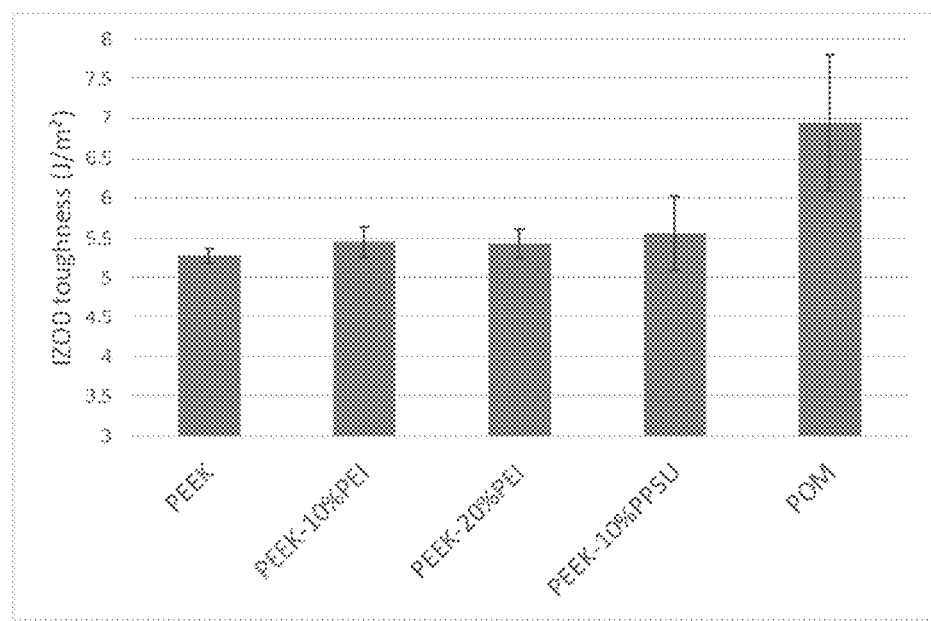
FIG. 6 is a graph showing the IZOD impact toughness of the various compositions disclosed herein.

The IZOD impact toughness was measured according to ASTM D4812. The pendulum weight was set to produce 11 Joule of impact energy. The results are shown in FIG. 6.

Example 2

Figure 7:
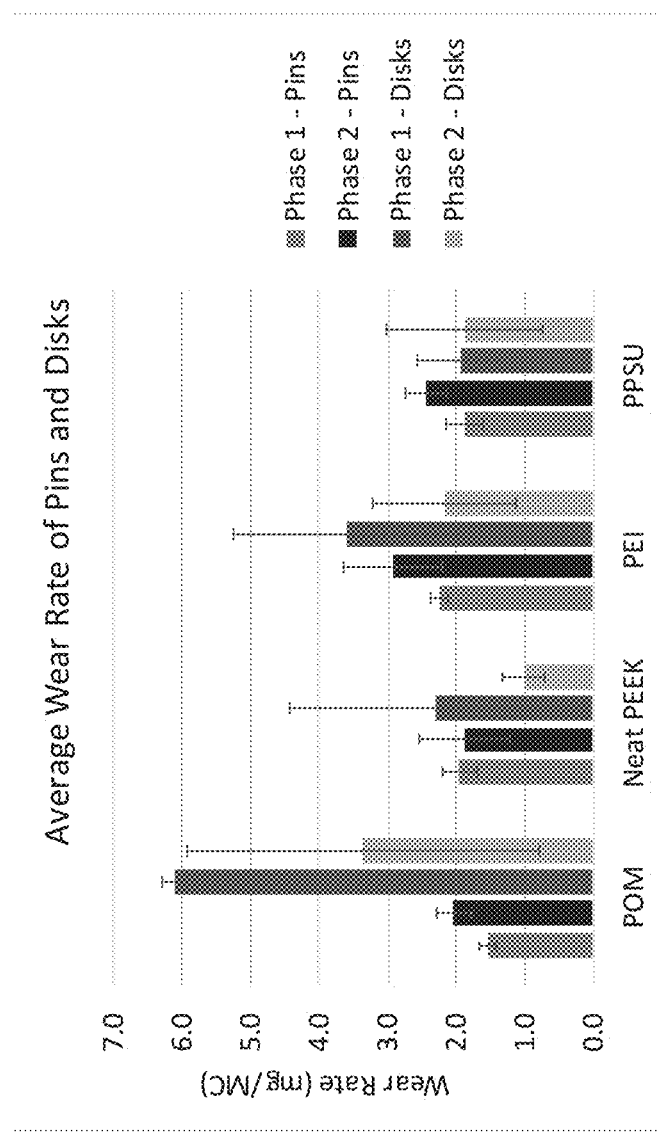
FIG. 7 is a graph showing the average wear rate of pins and disks after phase 1 ("as received") and phase 2 ("scratched")
Figure 8:
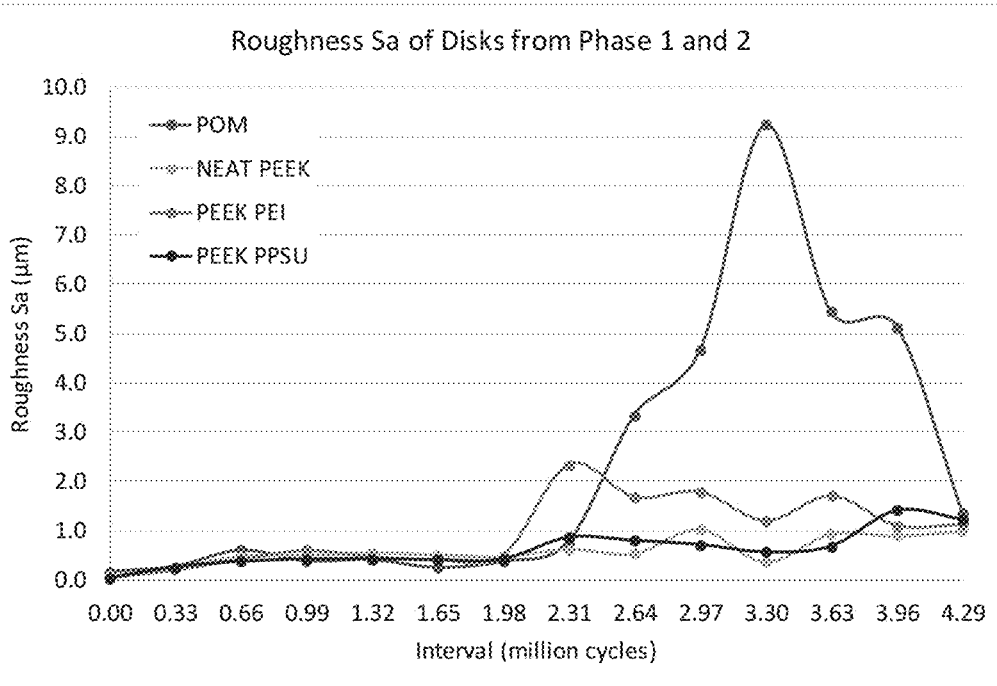
FIG. 8 is a graph showing the mean roughness Sa (µm) of the coupons comprising different polymers at each interval for Phase 1 (0.0-1.98 million cycles (MC)) and Phase 2 (2.31-4.29 MC)

Coupons were injection molded and tested for wear performance. The test assessed wear performance of XLK pins on PEEK coupons, PEEK/PPSU coupons, PEEK/PEI coupons, and POM coupons with scratching (phase 1) and without scratching (phase 2) of the coupons. The wear rate of the pins and coupons from both Phase 1 and 2 are summarized in FIG. 7. The wear rate for the XLK pins or the coupons was not significantly different within each sample type (i.e., POM Phase 1 vs Phase 2) before (Phase 1) and after (Phase 2) scratching the coupons. FIG. 8 summarizes the average roughness Sa of the four groups for the duration of the study. The disks were scratched for Phase 2 of testing after the 1.98 MC interval. The 2.31 MC interval data point is the roughness measurement after scratching the coupon and before Phase 2 of testing.

The Hostaform POM, KT-880-NT neat PEEK (Solvay), PEEK/10% PPSU, PEEK/20% PEI coupons were injection molded. They coupons were used as-molded except for the elimination of the gate and flashing and the addition of two through holes for alignment to the test fixture and have not been sterilized. The coupons were approximately 1.38 inches in diameter and 0.17 inches thick and mounted into custom made POD fixtures.

XLK polyethylene pins were used for wear testing. The articulating end of each pin had a fly cut surface topography machined on it. All pins had a diameter of 0.39 inches and a length of 0.9 inches. Eleven XLK pins were used for the wear testing and three were used for (unloaded) soak controls.

The test was performed using Paul-type loading with 330 N max load for 1.98 million cycles (MC) in bovine calf serum lubricant. Gravimetric assessment of the samples, using soak controls per WI-6071, calculates the wear at each interval.

Pins moved in a 10 mm by 10 mm (X-Y) square pattern. A Paul loading cycle (J. Paul, Proc. Inst. Mech. Eng., 181, 8-15, 1967) applies a peak of 330 N and a frequency of 1.6 Hz.

Each data collection interval was 0.33 million cycles (MC). At the end of each interval, used lubricant was discarded and new lubricant was added.

Each sample pair (poly pin+disk) were rotated to a new station for each interval.

Bovine serum (HyClone Laboratories Inc., Logan Utah, lot #AC10256479 was diluted to 90% (total protein concentration 62.1 mg/mL) following WI-0536. The serum contained 0.2% sodium azide and 20 mM EDTA as a preservative and calcium phosphate stabilizer, respectively.

Polyethylene pins were cleaned prior to beginning the test and between each interval.

The pins and disks were not pre-soaked prior to testing. The pins and disks were stored in RO water at room temperature between Phase 1 and 2 of testing.

Data collected after each test interval:

Gravimetric weighing of the pins was conducted using an XPE205 balance (Mettler Toledo, Columbus Ohio; Gage #9009170060000) per 103499701. Gravimetric weighing of the disks was conducted using an XP205 balance (Mettler Toledo, Columbus Ohio; Gage #9009140060000) per WI-6071.

Non-contact interferometry measurements were performed on the disks at the start of the test and after each interval using the Zygo NewView 8300 (Middlefield Conn., Gage #2077520050000). Feedback data was collected each interval and stored. Wear rates were calculated using a best-fit linear regression through the data, excluding the 0 cycle, 0 wear data point. Any exclusion of data from this analysis was accompanied by supporting evidence of assignable cause. Statistical comparison of the XLK pin and disk mean wear rates was made using a One-Way ANOVA with Tukey comparison test ($\alpha=0.2$).

Phase 1 Results

Figure 9:
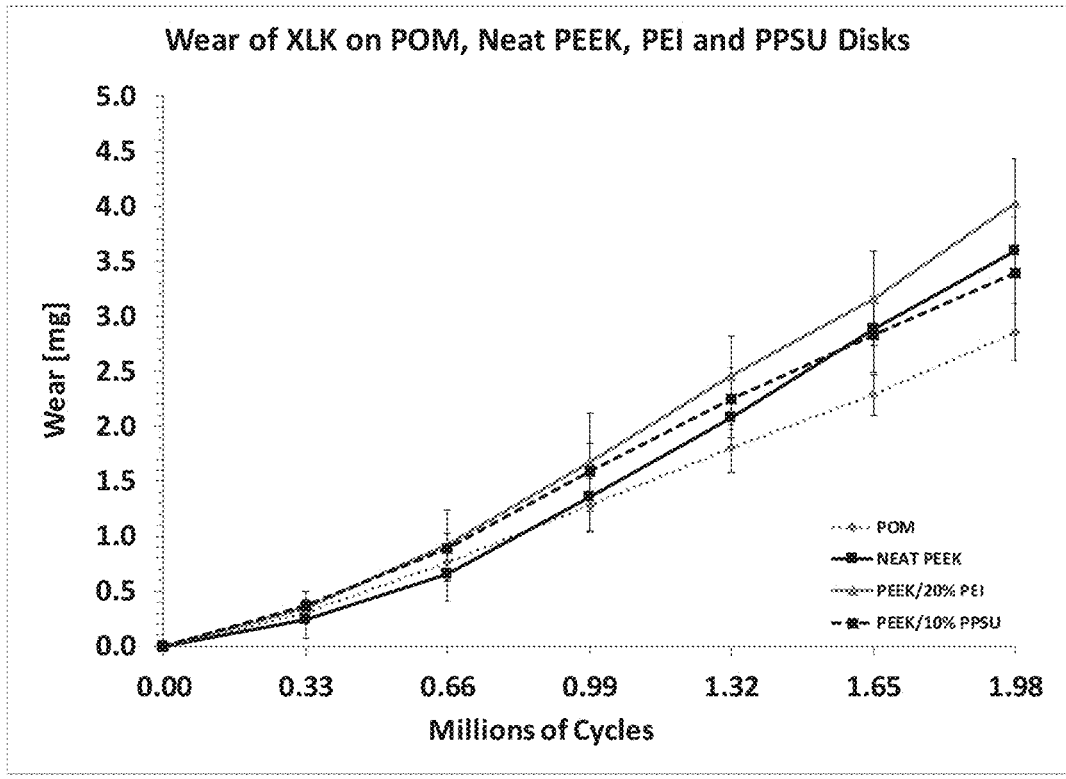
FIG. 9 is a graph showing the mean cumulative pin wear per interval for pins comprising POM, PEEK, PEEK/20% PEI, or PEEK/10% PPSU.
Figure 10:
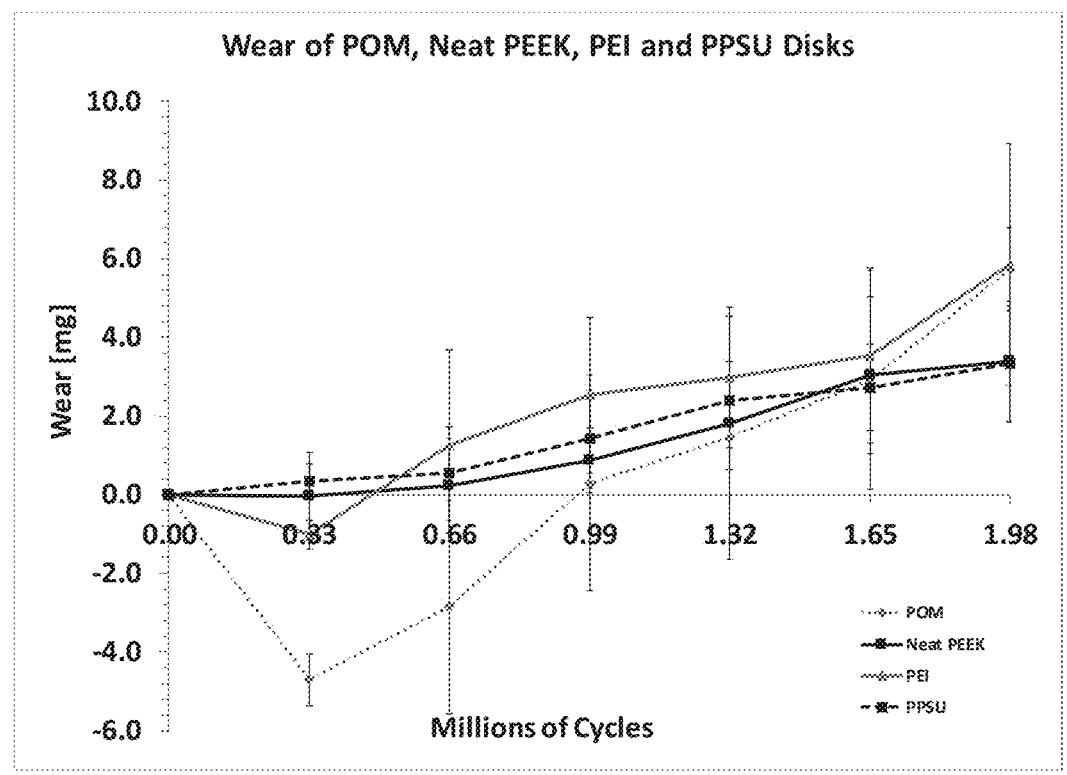
FIG. 10 is a graph showing the cumulative disk wear per interval for disks comprising POM, PEEK, PEEK/20% PEI, or PEEK/10% PPSU.
Figure 11:
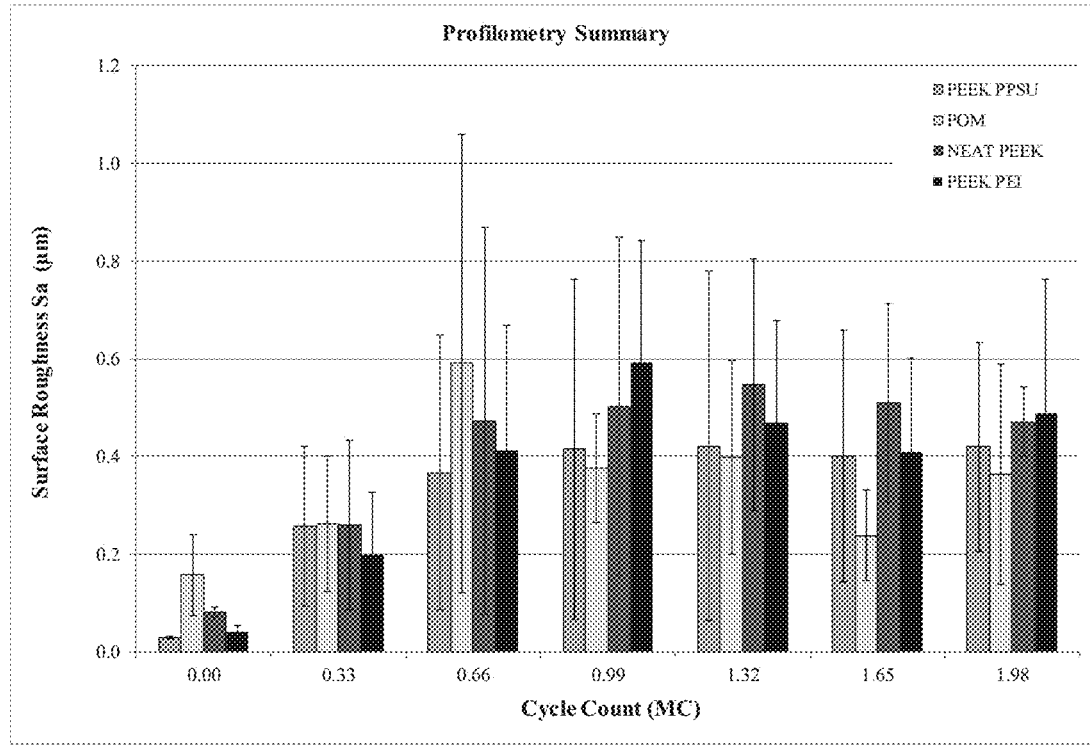
FIG. 11 is a graph showing the counterface surface roughness for various disks comprising POM, PEEK, PEEK/20% PEI, or PEEK/10% PPSU.

FIGS. 9 and 10 summarize the mean cumulative wear data. FIG. 9 shows the wear rate of the pin. FIG. 10 shows the wear rate of the disk. Counterface surface roughness of the disks using the Zygo interferometer is summarized in FIG. 11.

Figure 12:
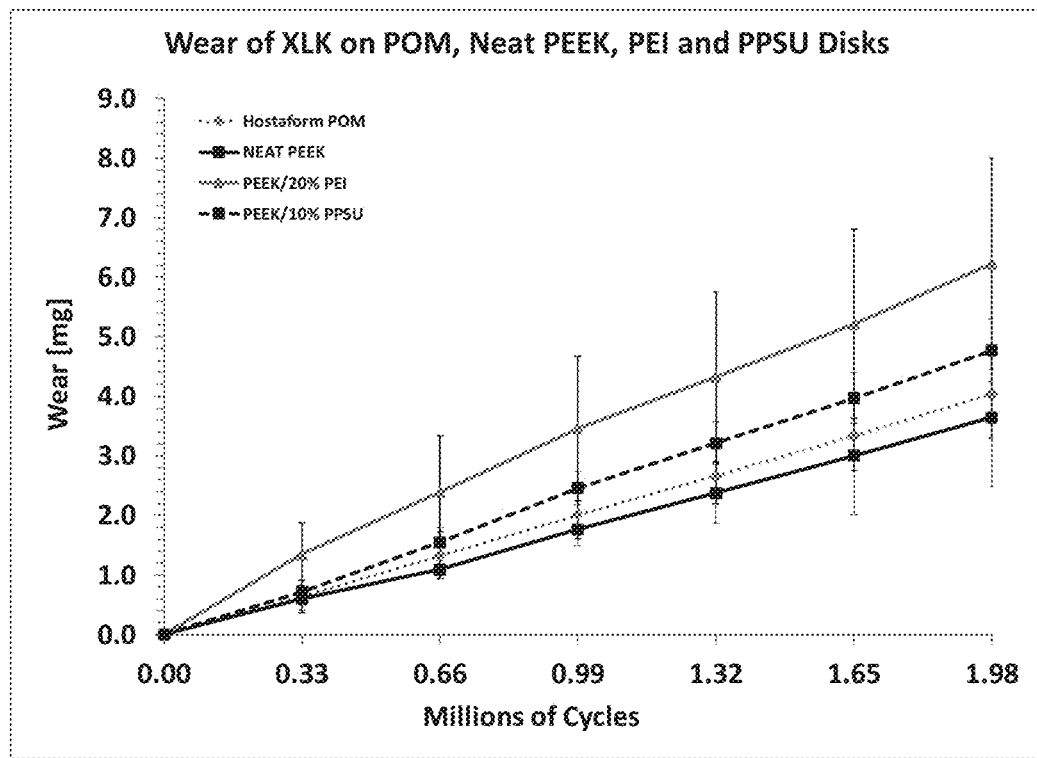
FIG. 12 is a graph showing the mean cumulative pin wear per interval as the pin interacts with disks comprising POM, PEEK, PEEK/20% PEI, or PEEK/10% PPSU.
Figure 13:
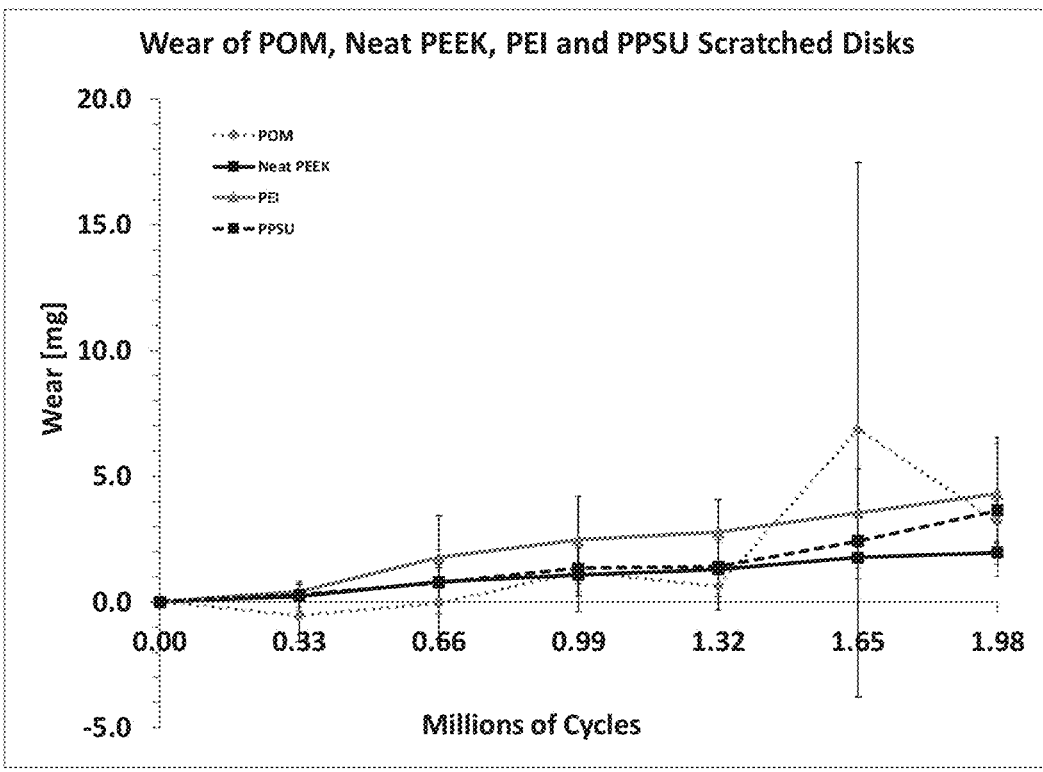
FIG. 13 is a graph showing the mean cumulative disk wear per interval as each disk interacts with a pin.
Figure 14:
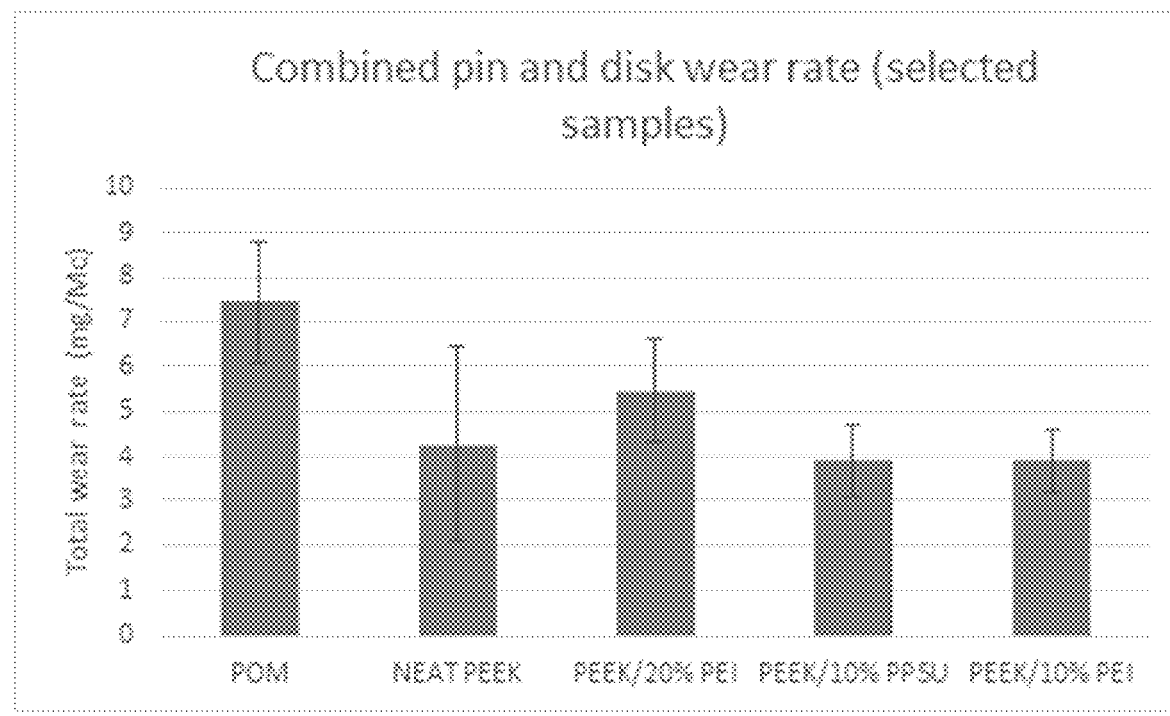
FIG. 14 is a graph showing the combined pin and disk wear rate.
Figure 15:
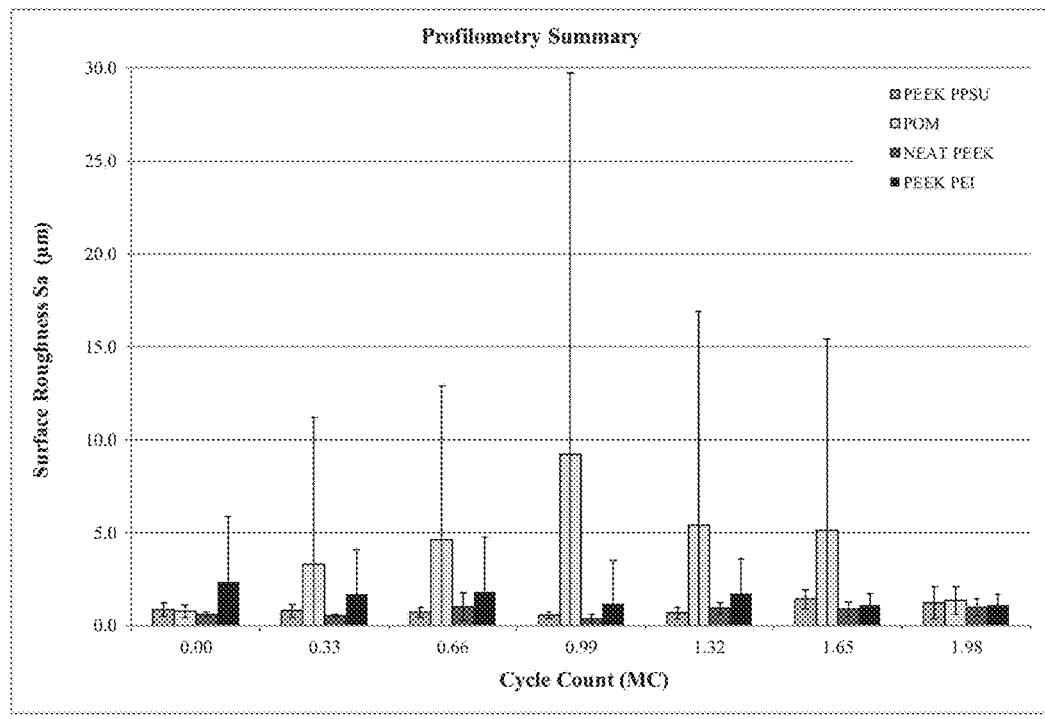
FIG. 15 is a graph showing the counterface surface roughness of the disks using an interferometer after subsequent cycle counts.

Phase 2 Results:

FIGS. 12 and 13 summarize the mean cumulative wear data. FIG. 12 shows the wear of the pin on the disks. FIG. 13 shows the wear of the disks. FIG. 14 shows the combined loss from the disks and the pin couples. Counterface surface roughness of the disks using the Zygo interferometer is summarized in FIG. 15.

Wear rates in mg/MC (MC=million cycles) (80% CI) and statistical outcome (shared letter=statistically equivalent) for the four sample groupings (mean±80% CI) are provided in Table 1.

TABLE 1

The wear rate (±80% CI):

| Part | Group | Wear Rate (mg/MC) | 80% CI |
|---|---|---|---|
| Pin | XLK HOSTAFORM POM (MT12-U03) | 1.54 | 0.13 |
|  | XLK HOSTAFORM POM (MT2-U06) | 1.2 | 0.2 |
|  | XLK NEAT PEEK | 1.95 | 0.26 |
|  | XLK PEEK-10% PEI | 2.1 | 0.2 |
|  | XLK PEEK-20% PEI | 2.24 | 0.14 |
|  | XLK PEEK-10% PPSU | 1.87 | 0.26 |
| Disk | HOSTAFORM POM DISKS (MT12-U03) | 6.12 | 0.18 |
|  | HOSTAFORM POM DISK (MT2-U06) | 3.5 | 0.5 |
|  | NEAT PEEK DISKS | 2.29 | 2.15 |
|  | PEEK-10% PEI DISKS | 1.8 | 0.6 |

TABLE 1-continued

The wear rate (±80% CI):

| Part | Group | Wear Rate (mg/MC) | 80% CI |
|------|-------|-------------------|--------|
|      | PEEK-20% PEI DISKS | 3.61 | 1.63 |
|      | PEEK-10% PPSU DISKS | 1.94 | 0.64 |

Example 3

Fatigue Testing

Figure 16:
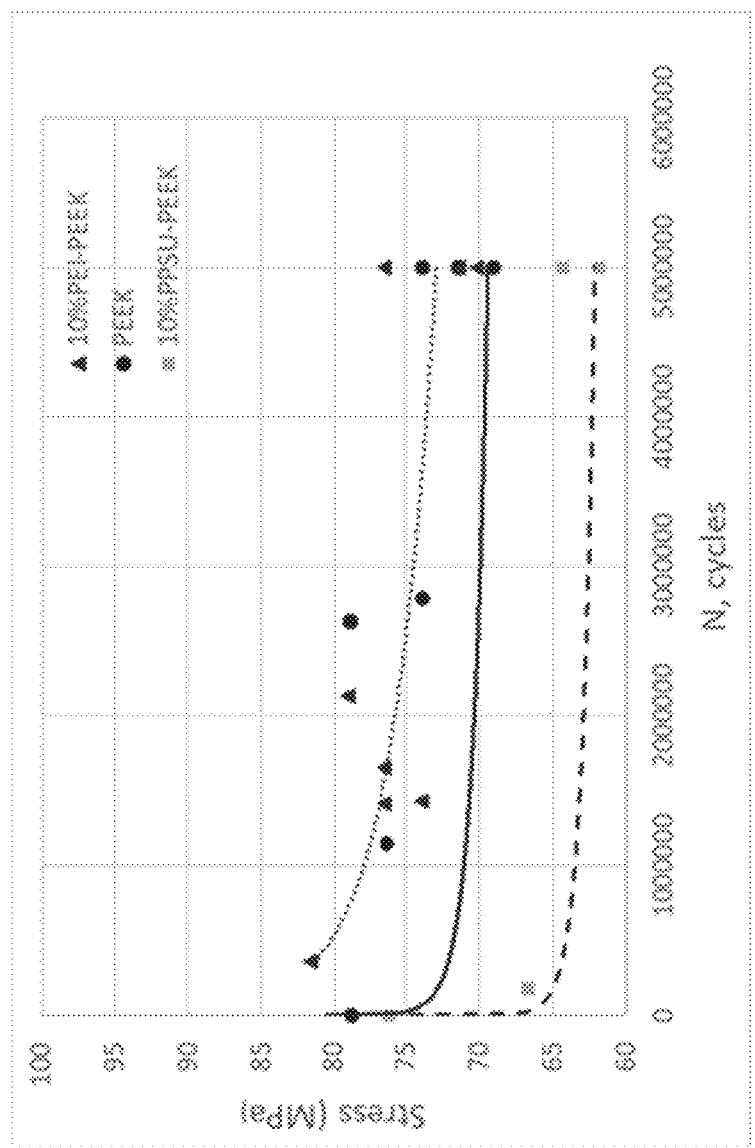
FIG. 16 is a graph showing fatigue testing of disks comprising PEEK, PEEK/10% PEI, or PEEK/10% PPSU.

Tension-tension fatigue testing of dog-bone samples as described in FIG. 1 was performed according to ASTM D3479/D3479M. Each cycle at the given stress level was carried out at 2 Hertz and to 5 million cycles. Discs formed from PEEK, PEEK with 10% PEI, and PEEK with 10% PPSU were analyzed. The results are shown in FIG. 16.

Figure 17:
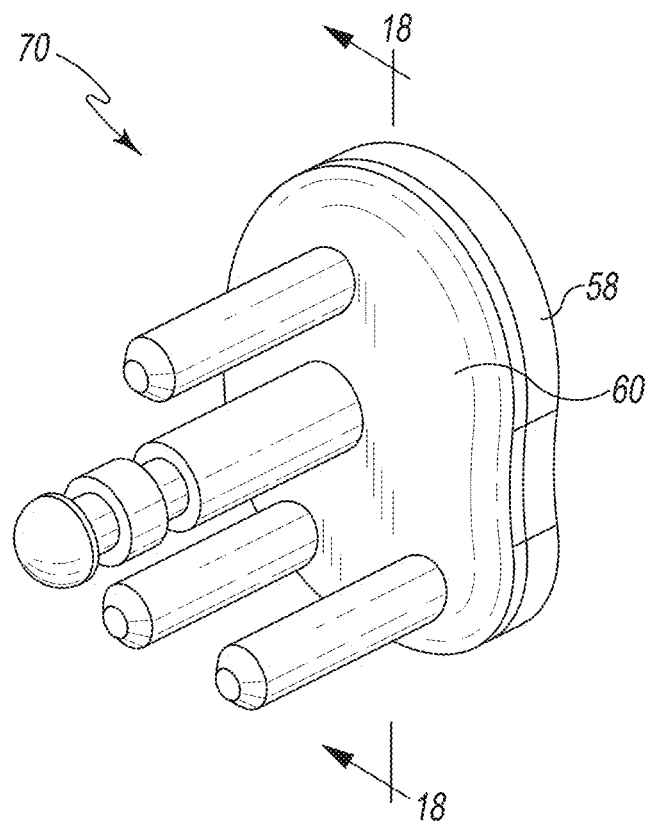
FIG. 17 is a perspective view of a glenoid component of a shoulder prosthesis.
Figure 18:
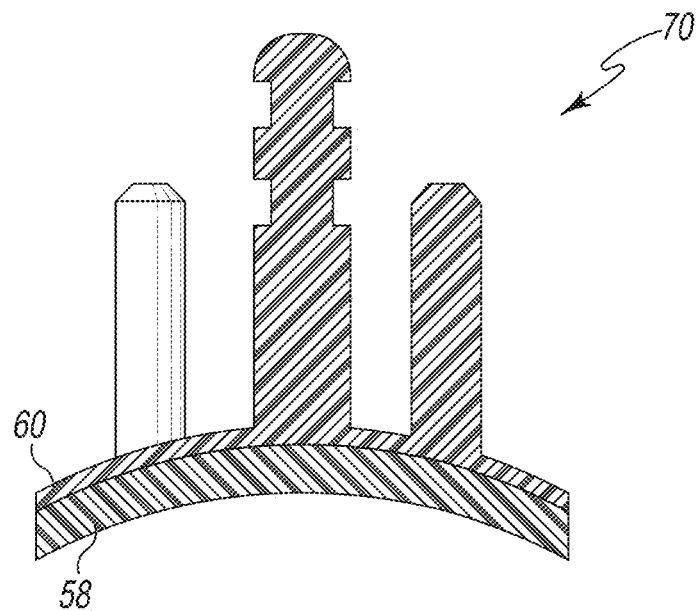
FIG. 18 is a cross-sectional view taken along the line 18-18 of FIG. 17, as viewed in the direction of the arrows.

As alluded to above, other orthopaedic components may be designed and fabricated in a similar manner to the femoral component 12. For example, as shown in FIGS. 17 and 18, a glenoid component 70 of a shoulder prosthesis may include an articular layer 58 and a support layer 60. Although not shown, a humeral component of a reverse shoulder prosthesis could also be designed and fabricated with an articular layer 58 and a support layer 60.

Figure 19:
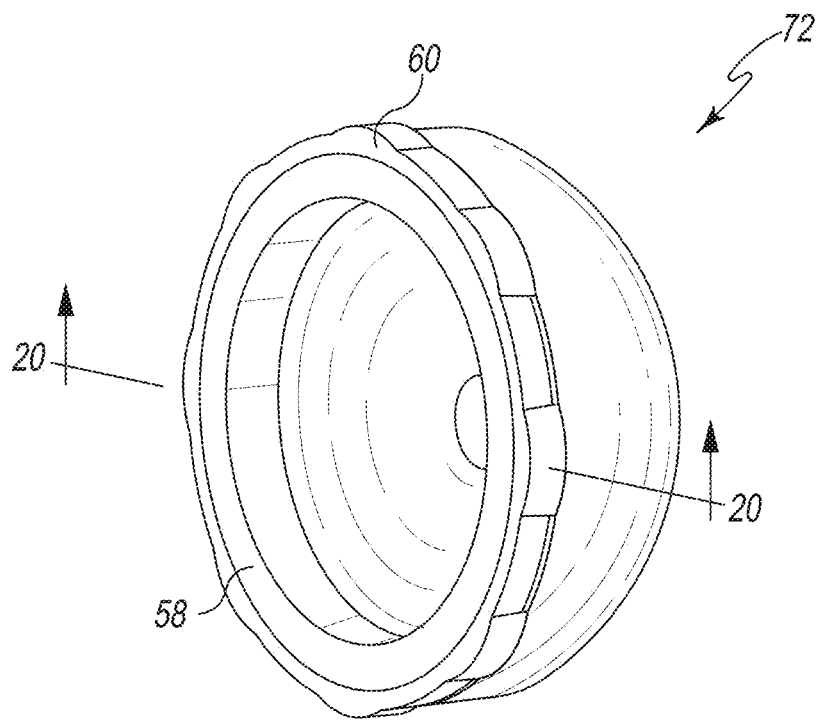
FIG. 19 is a perspective view of an acetabular component of a hip prosthesis.
Figure 20:
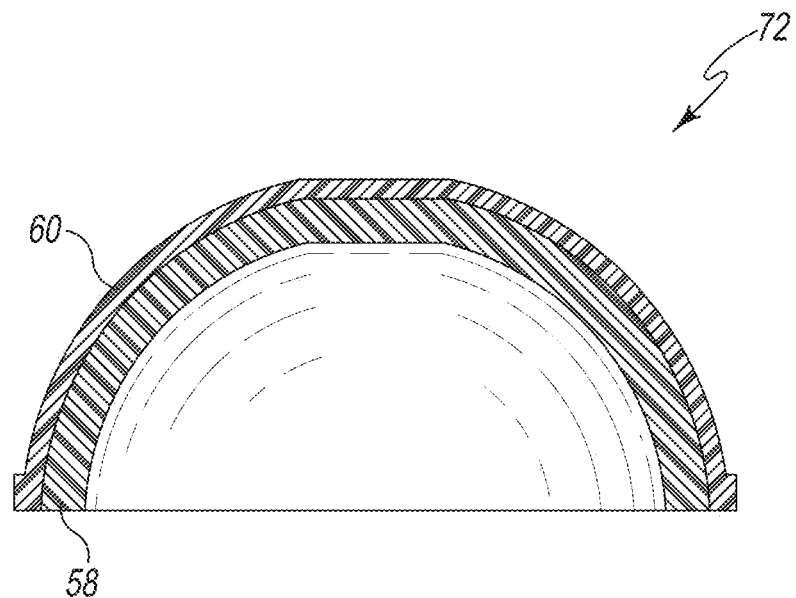
FIG. 20 is a cross-sectional view taken along the line 20-20 of FIG. 19, as viewed in the direction of the arrows.

Further, as shown in FIGS. 19 and 20, an acetabular component 72 of a hip prosthesis may include an articular layer 58 and a support layer 60. It should be appreciated that such an acetabular cup 72 may be configured for implantation in the acetabulum of a patient with or without the use of a separate acetabular shell.

Figure 21:
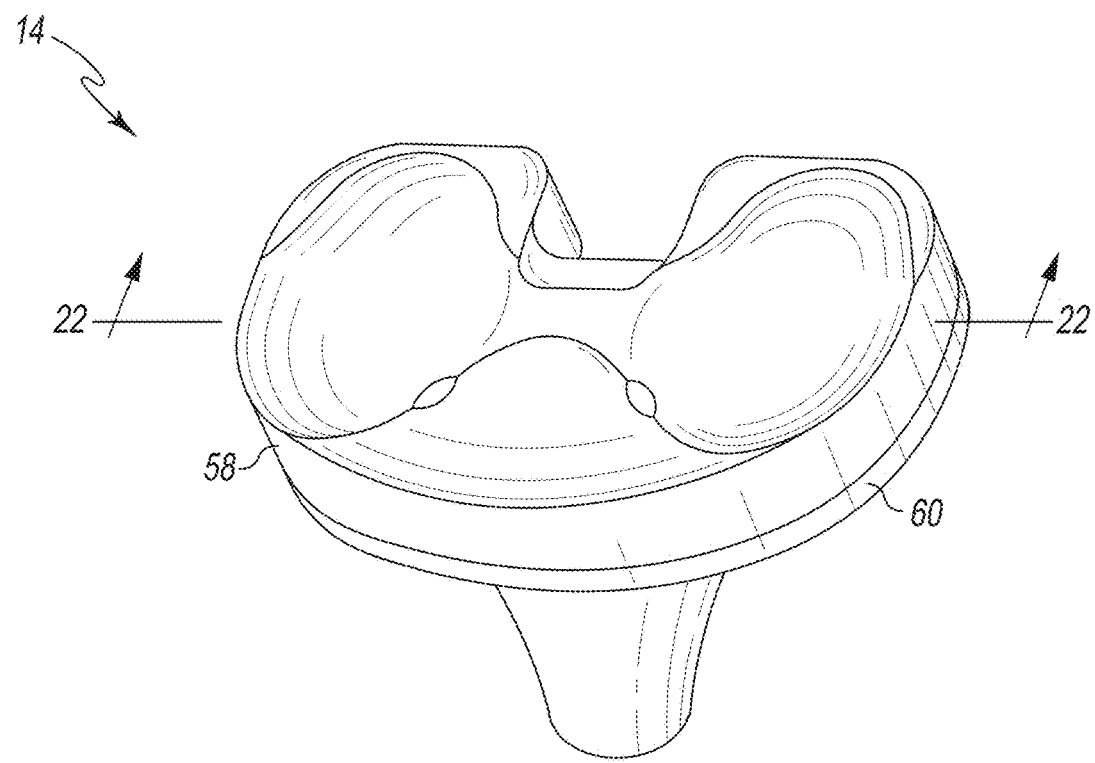
FIG. 21 is a perspective view of another embodiment of the tibial component of FIG. 1.
Figure 22:
FIG. 22 is a cross-sectional view taken along the line 22-22 of FIG. 21, as viewed in the direction of the arrows.
Figure 22:
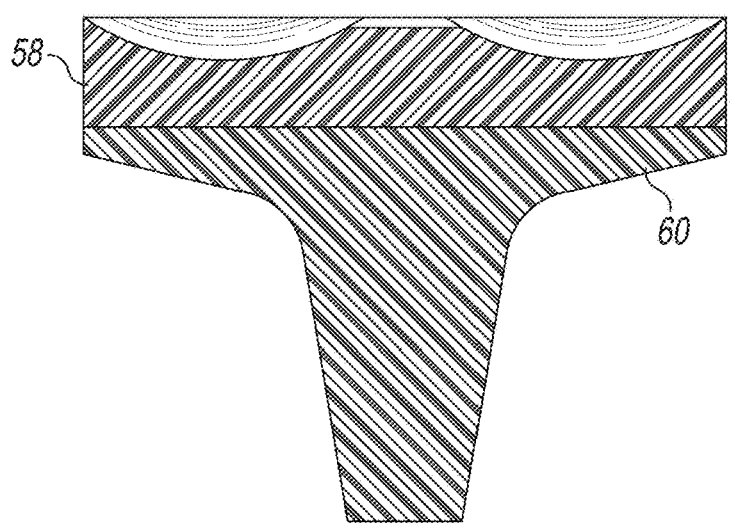

As shown in FIGS. 21 and 22, the tibial component 14 may be designed and fabricated with an articular layer 58 and a support layer 60. It should be appreciated that such an embodiment of the tibial component 12 may be configured for implantation in the tibia of a patient with or without the use of a tibial tray 16.

Figure 23:
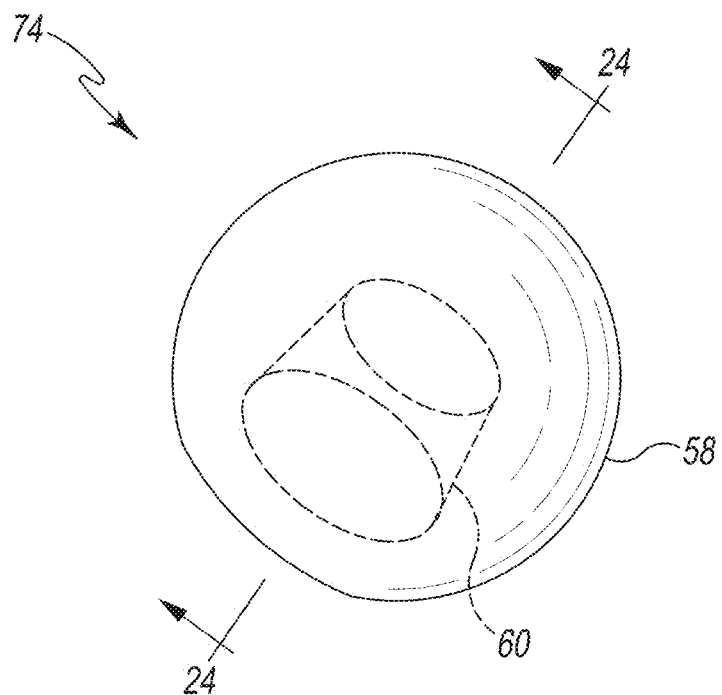
FIG. 23 is a perspective view of a head component of a hip prosthesis or a shoulder prosthesis.
Figure 24:
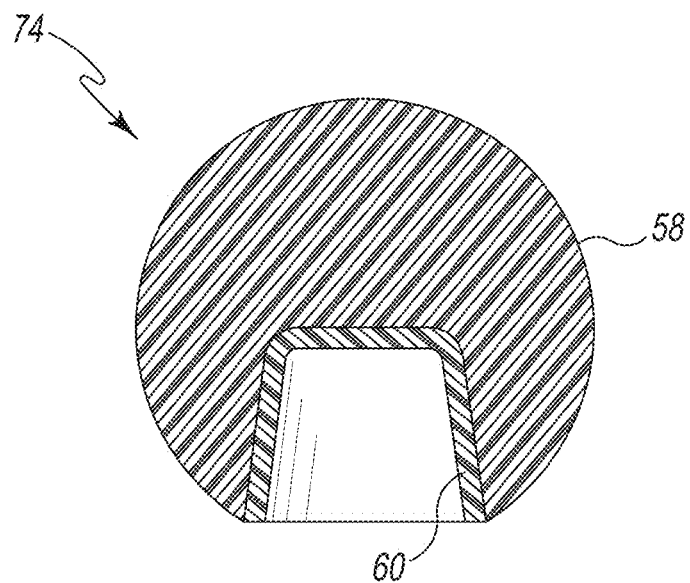
FIG. 24 is a cross-sectional view taken along the line 24-24 of FIG. 23, as viewed in the direction of the arrows.

Yet further, as shown in FIGS. 23 and 24, a head component 74 of either a hip prosthesis or shoulder prosthesis may be designed and fabricated with an articular layer 58 and a support layer 60. Although not shown, a glenosphere component of a reverse shoulder prosthesis could also be designed and fabricated with an articular layer 58 and a support layer 60.

Although additional examples of orthopaedic components that may be designed and fabricated with an articular layer 58 and a support layer 60 are shown in FIGS. 17-24, other orthopaedic components may also be designed and fabricated in such a manner including hip stems, humeral components of a shoulder prosthesis, components of an ankle prosthesis, components of an extremity prosthesis, or the like.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic knee prosthesis system, comprising:
    a tibial component configured to be implanted on a proximal end of a patient's tibia, the tibial component including a concave bearing surface, and
    a femoral component configured to be implanted on a distal end of a patient's femur, the femoral component comprising a femoral condyle having (i) an articular layer that includes an articulation surface that is curved in a sagittal plane and configured to articulate with the concave bearing surface of the tibial component, and (ii) a support layer that includes a bone-facing surface positioned opposite the articulation surface and configured to engage the distal end of the patient's femur,
    wherein the articular layer of the femoral component comprises a polyetheretherketone (PEEK) homopolymer, and
    wherein the support layer comprises (i) a reinforcement fiber and (ii) a homopolymer, a copolymer, or a mixture thereof.

2. The orthopaedic prosthesis system of claim 1, wherein the articular layer further comprises a polysulfone, a polyimide, or a mixture thereof.

3. The orthopaedic prosthesis system of claim 2, wherein the PEEK is about 75% to about 95% by weight of the articular layer.

4. The orthopaedic prosthesis system of claim 1, wherein the support layer comprises a polyaromatic ether homopolymer.

5. The orthopaedic prosthesis system of claim 1, wherein the support layer comprises a polyacetal copolymer.

6. The orthopaedic prosthesis system of claim 5, wherein the polyacetal copolymer is a polyoxymethylene copolymer.

7. The orthopaedic prosthesis system of claim 6, wherein the support layer comprises at least about 80% polyoxymethylene.

8. The orthopaedic prosthesis system of claim 6, wherein the reinforcement fiber is a glass fiber or a carbon fiber.

9. An orthopaedic knee prosthesis, comprising:
    a femoral component comprising a femoral condyle having (i) an articular layer that includes an articulation surface that is curved in a sagittal plane and configured to engage a tibial component, and (ii) a support layer that includes a bone-facing surface positioned opposite the articulation surface and configured to engage a distal end of a patient's femur,
    wherein the articular layer is constructed of a composite including a blend of a polyetheretherketone (PEEK) homopolymer and a polysulfone, a polyimide, or a mixture thereof, and
    wherein the articular layer has a yield strength of at least about 100 MPa.

10. The orthopaedic knee prosthesis of claim 9, wherein the articular layer is substantially free of fiber.

11. The orthopaedic knee prosthesis of claim 10, wherein the articular layer has a tensile modulus of at least about 4,000 MPa.

12. The orthopaedic knee prosthesis of claim 11, wherein the articular layer has an IZOD toughness of at least 5 J/m$^2$.

13. The orthopaedic knee prosthesis of claim 9, wherein the PEEK is about 75% to about 95% by weight of the articular layer.

\* \* \* \* \*